United States Patent [19]

Numata et al.

[11] Patent Number: 4,824,474
[45] Date of Patent: Apr. 25, 1989

[54] QUINOLINE DERIVATIVES AND HERBICIDAL COMPOSITIONS AND METHOD OF USE THEREOF

[75] Inventors: Tatsuo Numata; Masataka Hatanaka, Both of Funabashi; Junichi Watanabe, Narashino; Takasi Ikai, Tokyo; Tsutomu Nawamaki, Yono; Kenji Hattori, Urawa, all of Japan

[73] Assignee: Nissan Chemical Industries Ltd., Tokyo, Japan

[21] Appl. No.: 69,022

[22] Filed: Jul. 1, 1987

Related U.S. Application Data

[62] Division of Ser. No. 882,408, Jul. 7, 1986, Pat. No. 4,696,694.

[30] Foreign Application Priority Data

Jul. 25, 1985 [JP] Japan .................................. 60-164407
Jan. 16, 1986 [JP] Japan .................................... 61-6979
May 26, 1986 [JP] Japan .................................. 61-120455

[51] Int. Cl.$^4$ ..................... A01N 43/50; C07D 401/04
[52] U.S. Cl. ........................................ 71/92; 546/167; 546/15; 546/115
[58] Field of Search ....................... 546/167, 15; 71/92

[56] References Cited

U.S. PATENT DOCUMENTS 4,459,408 7/1984 Maulding et al. ................... 546/167
4,614,535 9/1986 Schmierer et al. ...................... 71/92

*Primary Examiner*—David B. Springer
*Attorney, Agent, or Firm*—Oblon, Fisher, Spivak, McClelland & Maier

[57] ABSTRACT

A pyridine derivative having the formula:

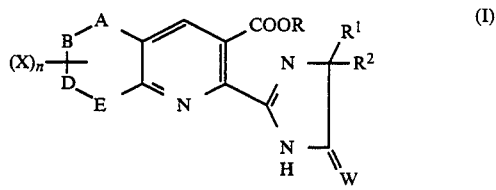

wherein one of A, B, D and E is oxygen, sulfur, —SO—, —SO$_2$—, —NR$^3$—,

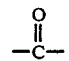

or =CH— with the rest being all carbon atoms; X is halogen, C$_1$-C$_4$ alkyl, C$_1$-C$_4$ alkoxy, C$_1$-C$_4$ haloalkyl, C$_1$-C$_4$ haloalkoxy, C$_1$-C$_4$ alkylthio, C$_1$-C$_4$ haloalkylthio, C$_1$-C$_4$ alkoxycarbonyl, C$_1$-C$_4$ alkylthioalkyl, tetrahydrothiopyranyl, hydroxyl, CF$_3$, phenyl or pyridyl; n is an integer of from 0 to 6,; W is oxygen or sulfur; R is hydrogen, di-lower alkylimino, C$_1$-C$_5$ alkyl, C$_2$-C$_5$ alkenyl, C$_2$-C$_5$ alkynyl, C$_4$ or C$_5$ oxacycloalkyl, C$_2$-C$_5$ mono-, di- or tri-haloalkenyl, C$_2$-C$_5$ haloalkynyl, glycidyl, furfuryl, alkylthioalkyl, C$_3$-C$_6$ cycloalkyl or a cation R$^1$ is C$_1$-C$_4$ alkyl, R$^2$ is C$_1$-C$_4$ alkyl or C$_3$-C$_6$ cycloalkyl, or R$^1$ and R$^2$ together with the adjacent carbon atom, form C$_3$-C$_6$ cycloalkyl; and R$^3$ is hydrogen or C$_1$-C$_3$ alkyl.

7 Claims, No Drawings

QUINOLINE DERIVATIVES AND HERBICIDAL COMPOSITIONS AND METHOD OF USE THEREOF

This is a division of application Ser. No. 06/882,408, filed July 7, 1986, U.S. Pat. No. 4,696,694.

The present invention relates to novel 2-(2-imidazolin-2-yl)pyridine-3-carboxylic acid derivatives, a process for their production and a herbicidal composition containing such derivatives.

It is generally accepted that the costs for the use of a herbicide are dependent on the amount of the active ingredient required per a unit surface area, and a development of a new herbicide which is effective at a low dose, has been desired. On the other hand, with the conventional herbicides, adverse effects are sometimes given to the crop plants during the use, and researches for the compounds having high herbicidal activities at a low dose and having high selectivity as between the crop plants and unwanted weeds, have been conducted for many years. For instance, European Patent Publications No. 0041623 and No. 0127883 disclose 2-(2-imidazolin-2-yl)pyridine-3-carboxylic acid derivatives. However, these derivatives do not necessarily satisfy the above requirements.

The present inventors have conducted extensive researches for many years, and have finally found that the compounds of the present invention have remarkable herbicidal activities as compared with conventional herbicides, and yet many of the compounds of the present invention are practically useful as having superior selectivity for crop plants particularly for leguminous plants such as soybean (*Glysine max*), peanut (*Arachis hypogaea*), alfalfa (*Medicage sativa*), French bean (*Phaseolus vulgaris*), adzuki bean (*Vigna angularis*) and pea (*Pisum sativum*). Further, it has been found that they have excellent herbicidal activities against important weeds such as morning glory (*Ipomoea spps.*), Johnsongrass (*Sorghum halepense*), velvetleaf (*Abutilon theophrasti*) and prickly sida (*Sida spinosa*), and they have a wide herbicidal spectrum including broad leaf weeds, gramineous weeds and cyperaceous weeds and have a wide range of application period ranging from soil treatment to foliage treatment. The present invention has been accomplished on the basis of these discoveries.

Namely, with the compounds of the present invention, the dose of the active ingredient per unit surface area can be remarkably reduced as compared with the conventional herbicides, and the phytotoxicity to the crop plants is substantially less as compared with the conventional herbicides. Thus, the economical advantage is substantial. Further, with the compounds of the present invention, the danger of environmental pollution by the application of the herbicide in a substantial amount can be minimized, and adverse effects to other crop plants due to the residual effects are minimum.

The present invention provides a pyridine derivative having the formula:

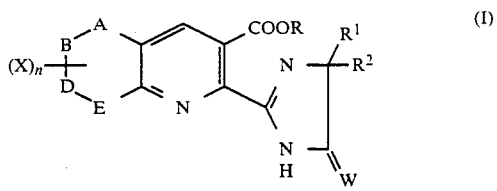 (I)

wherein one of A, B, D and E is an oxygen atom, a sulfur atom, —SO—, —SO$_2$—, —NR$^3$—,

or =CH— with the rest being all carbon atoms, provided that when one of A, B, D and E is =CH—, one double bond is present in the ring constituted by A, B, D and E, and when one of A, B, D and E is an oxygen atom, a sulfur atom, —SO—, —SO$_2$—, —NR$^3$— or

one double bond may or may not be present in the ring; X is a halogen atom, a C$_1$-C$_4$ alkyl group, a C$_1$-C$_4$ alkoxy group, a C$_1$-C$_4$ haloalkyl group, a C$_1$-C$_4$ haloalkoxy group, a C$_1$-C$_4$ alkylthio group, a C$_1$-C$_4$ haloalkylthio group, a C$_1$-C$_4$ alkoxycarbonyl group, a C$_1$-C$_4$ alkylthioalkyl group, a tetrahydrothiopyranyl group, a hydroxyl group, a CF$_3$ or a phenyl or pyridyl group (which may be substituted by C$_1$-C$_4$ alkyl, C$_1$-C$_4$ alkoxy, C$_1$-C$_4$ alkylthio, CF$_3$, nitro or halogen); n is an integer of from 0 to 6, and when n is an integer of from 2 to 6, the plurality of X may be the same or different; W is an oxygen atom or a sulfur atom; R is a hydrogen atom, a di-lower alkylimino group, a C$_1$-C$_5$ alkyl group (which may be substituted by C$_1$-C$_3$ alkoxy, hydroxyl, C$_3$-C$_6$ halocycloalkyl, carboxyl, lower alkoxycarbonyl, cyano, dialkylphosphonyl, halogen, benzyloxy, tri-lower alkylammonium or phenyl which may be substituted by halogen, C$_1$-C$_4$ alkyl, C$_1$-C$_4$ alkoxy or nitro), a C$_2$-C$_5$ alkenyl group (which may be substituted by C-C$_3$ alkoxy, lower alkoxycarbonyl, two C$_1$-C$_3$ alkoxy or phenyl), a C$_2$-C$_5$ alkynyl group, a C$_4$ or C$_5$ oxacycloalkyl group, a C$_2$-C$_5$ mono-, di- or trihaloalkenyl group, a C$_2$-C$_5$ haloalkynyl group, a glycidyl group, a furfuryl group, an alkylthioalkyl group, a C$_3$-C$_6$ cycloalkyl group which may be substituted by C$_1$-C$_3$ alkyl, or a cation selected from the group consisting of an alkali metal ion, an alkaline earth metal ion, an ammonium ion or a quaternary ammonium ion; R$^1$ is a C$_1$-C$_4$ alkyl group, R$^2$ is a C$_1$-C$_4$ alkyl group or a C$_3$-C$_6$ cycloalkyl group, or R$^1$ and R$^2$ together with the adjacent carbon atom, form a C$_3$-C$_6$ cycloalkyl group which may be substituted by C$_1$-C$_3$ alkyl; and R$^3$ is a hydrogen atom or a C$_1$-C$_3$ alkyl group; or an optical isomer of the derivative when R$^1$ and R$^2$ are different from each other.

The compounds of the present invention are novel compounds not disclosed in any prior literature, and have excellent physiological activities as herbicides.

The present invention provides also a process for producing the compound of the formula I, which comprises (A) cyclizing a compound having the formula:

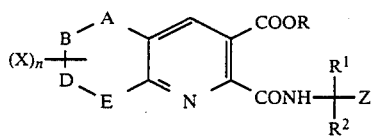

(II-a)

wherein A, B, D, E, X, n, R, R¹ and R² are as defined above, and Z is

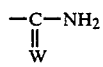

or —CN, wherein W is as defined above, and if necessary, subjecting the resulting cyclized product to hydrolysis, esterification, ester exchange or conversion to an alkali metal, alkaline earth metal, ammonium or quaternary ammonium salt; or (B) reacting a compound having the formula:

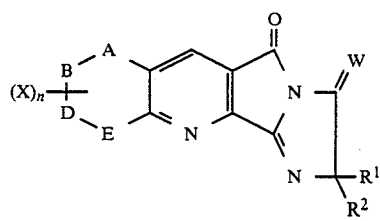

(II-b)

or

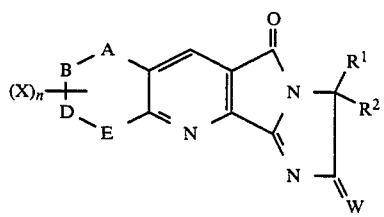

(II-c)

wherein A, B, D, E, X, n, W, R¹ and R² are as defined above, with an alcohol having the formula ROH wherein R is as defined above but other than a hydrogen atom, and if necessary, subjecting the resulting product to hydrolysis, esterification, ester exchange or conversion to an alkali metal, alkaline earth metal, ammonium or quaternary ammonium salt.

Further, the present invention provides a herbicidal composition comprising a herbicidally effective amount of a pyridine derivative of the formula I or its optical isomer, and a carrier therefore. The herbicidal composition may further contain another herbicide or agricultural chemical which is commonly employed.

Still further, the present invention provides a method for controlling weeds, which comprises applying to the weeds or to the locus of the weeds an effective amount of a pyridine derivative of the formula I or its optical isomer.

Now, the present invention will be described in detail.

The compounds of the formula I of the present invention may be readily prepared by the following reaction.

REACTION SCHEME 1

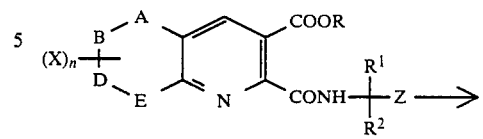

(II-a)

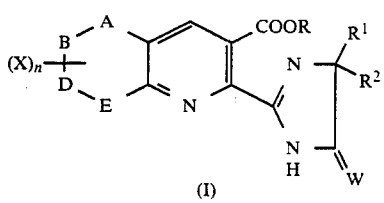

(I)

wherein Z is

and A, B, D, E, X, n, W, R, R¹ and R² are as defined above.

Namely, the compound of the formula II-a wherein R is a hydrogen atom and Z is

is heated in an aqueous solution containing from 1 to 50% (from 1 to 10 equivalent mols) of an alkali metal hydroxide or an alkaline earth metal hydroxide, such as sodium hydroxide, potassium hydroxide or magnesium hydroxide, at a temperature of from room temperature to 100° C., whereby a compound of the formula I wherein R is sodium, potassium, magnesium or calcium can be obtained. By neutralizing the product with a mineral acid such as hydrochloric acid or sulfuric acid, a compound of the formula I wherein R is a hydrogen atom can be obtained. Further, by treating the product with ammonia or an organic amine, a compound of the formula I wherein R is an ammonium ion or a quaternary ammonium ion can be obtained. Further, a compound of the formula I wherein R is a hydrogen atom may be esterified with an alcohol of the formula ROH wherein R is as defined above but other than a hydrogen atom, in the presence of an acid catalyst, to obtain compounds of the formula I having various R other than a hydrogen atom. Likewise, a compound of the formula I wherein R is a methyl group or an ethyl group may be obtained by treating a compound of the formula I wherein R is a hydrogen atom, with diazomethane in an inert solvent, or by treating it with methyl iodide, methyl chloride, methyl bromide, dimethyl sulfate, ethyl iodide, ethyl bromide, ethyl chloride, diethyl sulfate, triethyloxonium tetrafluoroborate or trimethyloxonium tetrafluoroborate. Further, the product may be subjected to ester exchange with an alcohol of the formula ROH where R is any one of various types as mentioned above other than a hydrogen atom, to obtain compounds of the formula I having various R other than a hydrogen atom.

In a similar manner, a compound of the formula II-a wherein R is an alkali metal ion, an alkaline earth metal ion, an ammonium ion or a quaternary ammonium ion, can be cyclized directly to obtain the corresponding compound of the formula I.

The starting compound of the formula II wherein R is a hydrogen atom can be prepared by the following method A.

METHOD A

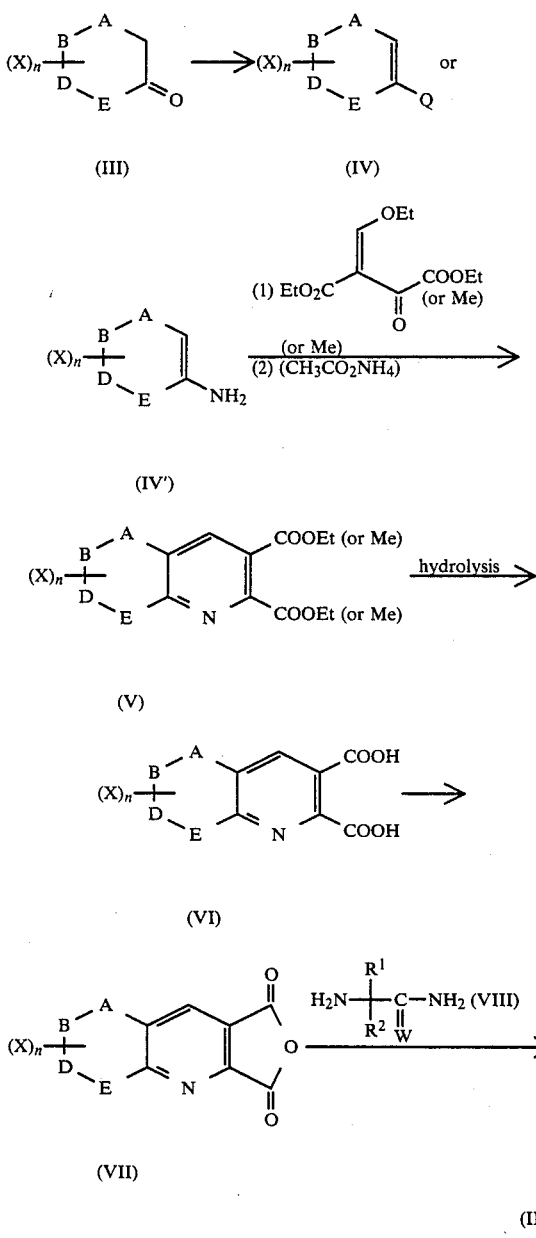

wherein Q is —N(CH₃)₂, —N(CH₂CH₃)₂,

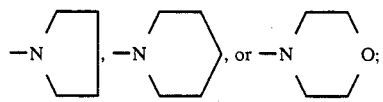

Z is

and A, B, D, E, X, W, n, R, R¹ and R² are as defined above.

Namely, the enamine compound of the formula IV can be obtained in good yield by reacting a compound of the formula III prepared in accordance with e.g. the Journal of Organic Chemistry, 36, 2077 (1971) or Journal of the American Chemical Society, 74, 1569 (1952), with a secondary amine (such as pyrrokidine, piperidine, morpholine, diethylamine or dimethylamine) in accordance with the method disclosed in e.g. Synthesis 368 (1978). This enamine compound of the formula IV is reacted with ethyl ethoxymethyleneoxaloacetate in a suitable solvent (such as ethanol, acetic acid or benzene), and then ammonium acetate is added and reacted thereto under heating and stirring, whereby diethyl pyridine-2,3-dicarboxylate of the formula V can be obtained in good yield.

Alternatively, a compound of the formula IV' wherein A is

can be prepared from a compound of the formula III wherein A is

in good yield in accordance with the method disclosed in e.g. Synthesis 902 (1983). Then, the pyridine-2,3-dicarboxylic acid diester of the formula V wherein A is

can be obtained in good yield by reacting the compound of the formula IV' wherein A is

with an ethoxymethyleneoxaloacetic acid ester in a suitable solvent (such as diethyl ether, ethanol, acetic acid or benzene) in accordance with Journal of the American Chemical Society, 73, 4380 (1951) or Journal of the American Chemical Society, 74, 1489 (1952).

Furthermore, the diester of the formula V wherein A is

may be reduced in a suitable solvent, preferably in diethyl ether, methanol or an aqueous solvent, by using a metal hydride such as sodium borohydride, to obtain a compound of the formula V wherein A is —CH(OH)—.

Still further, a compound of the formula V wherein E is —CH(OH)— can be obtained in accordance with e.g.

Journal of the American Chemical Society, 76, 1286 (1954) from a 5,6,7,8-tetrahydroquinoline derivative which can be prepared in accordance with e.g. Journal of the Chemical Society Chemical Communications, 133 (1982).

These compounds of the formula V wherein A or E is —CH(OH)— may be dehydrated by using a suitable dehydrating agent, preferably sulfuric acid, a sulfate or paratoluene sulfonic acid, to obtain compounds of the formula V wherein A or E is =CH—.

The diester of the formula V is treated with a water-alcohol solution containing at least two mols of an alkali metal hydroxide such as sodium hydroxide or potassium hydroxide to obtain the corresponding dicarboxylic acid of the formula VI. The dicarboxylic acid of the formula VI is then heated with acetic anhydride or trifluoroacetic anhydride at a temperature of from room temperature to the refluxing temperature, preferably at a temperature of from 60° to 100° C., to obtain the corresponding acid anhydride of the formula VII. This acid anhydride of the formula VII is reacted with an α-aminoamide of the formula VIII in a suitable solvent (such as acetonitrile, methylene chloride, pyridine or picoline), whereby a carboxylic acid amide derivative of the formula II-a wherein R is a hydrogen atom and Z is

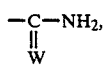

can be obtained. In some cases, the isomer carboxylic acid amide derivative of the formula II-a' wherein R is a hydrogen atom, and Z is

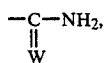

is produced as a by-product.

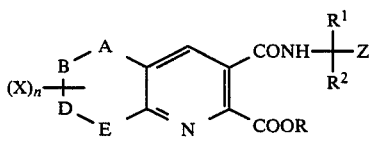

wherein R is a hydrogen atom, Z is

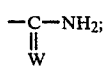

and A, B, D, E, X, W, n, $R^1$ and $R^2$ are as defined above.

REACTION SCHEME 2

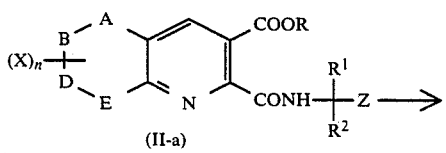

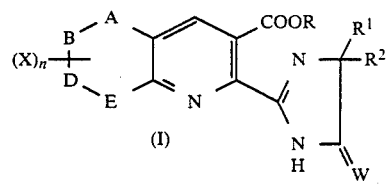

wherein R is a methyl group or an ethyl group, Z is

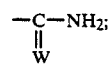

and A, B, D, E, X, W, n, $R^1$ and $R^2$ are as defined above.

Namely, a compound of the formula I wherein R is a methyl group or an ethyl group, can be obtained by treating a compound of the formula II-a wherein R is a methyl group or an ethyl group, with e.g. phosphorus pentachloride, sodium hydride, sodium methoxide or sodium ethoxide in an inert solvent such as benzene, hexane or ethyl ether.

Alternatively, a compound of the formula I wherein R is a methyl group or an ethyl group may be obtained by treating a compound of the formula II-a wherein R is a methyl group or an ethyl group, with a dehydrating condensation agent such as dicyclohexylcarbodiimide or acetic anhydride in a suitable solvent, preferably in dichloroethane, dichloromethane, chloroform, carbon tetrachloride, tetrahydrofuran or acetic acid.

The compound of the formula I wherein R is a methyl group or an ethyl group can be hydrolyzed to a compound of the formula I wherein R is a hydrogen atom.

Further, as described with reference to Reaction Scheme 1, the compound of the formula I wherein R is a hydrogen atom can be converted to various compounds of the formula I of the present invention by esterification, by ester exchange, or by neutralization with ammonia, an organic amine such as isopropyl amine, or an alkali metal or alkaline earth metal hydroxide such as sodium hydroxide, potassium hydroxide, magnesium hydroxide or calcium hydroxide.

In a similar manner, a compound of the formula II-a wherein R is other than a hydrogen atom, an alkali metal ion, an alkaline earth metal ion, an ammonium ion and the quaternary ammonium ion, can be cyclized directly to obtain the corresponding compound of the formula I.

The starting compound of the formula II-a wherein R is a methyl group or an ethyl group and Z is

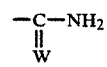

can be prepared in accordance with the following method B.

Method B-1

V or VII ⟶

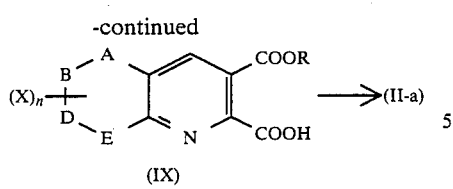 →(II-a)

(IX)

Method B-2

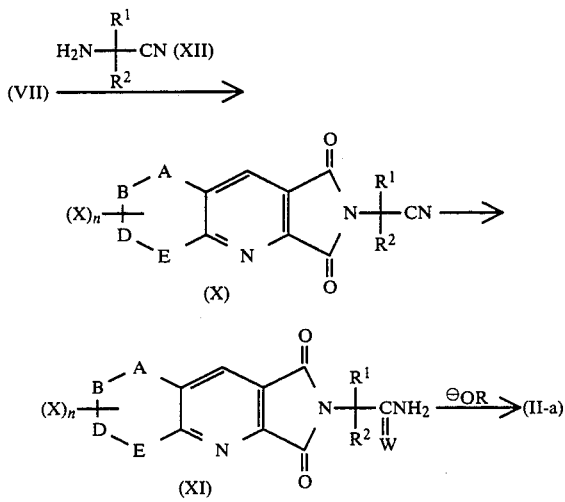

wherein R is a methyl group or an ethyl group; Z is

and A, B, D, E, X, W, n, R¹ and R² are as defined above.

Namely, a half ester of the formula IX wherein R is a methyl group or an ethyl group can be prepared either by the semi-hydrolysis of the corresponding diester of the formula V wherein R is a methyl group or an ethyl group, or by the methanol or ethanol decomposition of the acid anhydride of the formula VII. The compound of the formula IX wherein R is a methyl group or an ethyl group is converted by thionyl chloride to the acid chloride or by chloroformic acid ester to an active ester, followed by the reaction with an α-aminoamide of the formula VIII to obtain a compound of the formula II-a wherein R is a methyl group or an ethyl group, and Z is

Alternatively, the acid anhydride of the formula VII and the α-aminonitrile of the formula XII are reacted in an inert solvent, and after the removal of the solvent, heated in an acetic anhydride solvent in the presence of a catalytic amount of sodium acetate or potassium acetate, to obtain a compound of the formula X. Then, the compound of the formula X is treated with a strong acid such as sulfuric acid, if necessary, in a halogenated hydrocarbon solvent such as chloroform, methylene chloride or carbon tetrachloride, to obtain a compound of the formula XI wherein W is an oxygen atom. The compound of the formula XI wherein W is an oxygen atom is then treated with a methoxy or ethoxy anion in the presence of a methanol or ethanol, whereby a compound of the formula II-a wherein R is a methyl or ethyl group is obtainable.

In a similar manner, a compound of the formula II-a wherein R is other than a hydrogen atom, an alkali metal ion, an alkaline earth metal ion, an ammonium ion, and a quaternary ammonium ion, can be obtained directly from the corresponding compound.

REACTION SCHEME 3

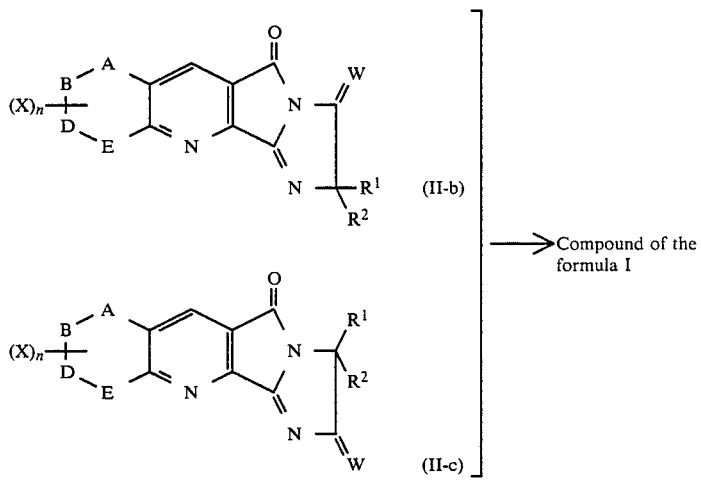

wherein A, B, D, E, X, W, n, R, R¹ and R² are as defined above.

Namely, a compound of the formula II-b or II-c is reacted with an alcohol of the formula ROH where R may be any one of various groups as identified above other than a hydrogen atom in an inert aprotic solvent such as tetrahydrofuran or dioxane at a temperature of from about 20° to 50° C., if necessary, in the presence of sodium hydride or an organic base such as triethylamine, as the catalyst, to obtain a compound of the formula I wherein R is other than a hydrogen atom.

Otherwise, a compound of the formula II-b or II-c is reacted in an alcohol solvent of the formula ROH wherein R is any one of various groups than a hydrogen atom at a temperature of from about 20° C. to the refluxing temperature, if necessary, with an addition of an alkali metal alkoxide such as sodium alkoxide (RONa)

or potassium alkoxide (ROK), or with an addition of an organic base such as DBU (1,8-diazabicyclo[5,4,0]-7-undecene), to obtain a compound of the formula I wherein R is other than a hydrogen atom.

The compound of the formula I can be converted by hydrolysis to a compound of the formula I wherein R is a hydrogen atom.

Further, as described with reference to Reaction Scheme 1, the compound of the formula I wherein R is a hydrogen atom can be converted to a compound of the formula I having various R by esterification, by ester exchange or by neutralization with ammonia, an organic amine such as isopropylamine or an alkali metal or alkaline earth metal hydroxide such as sodium hydroxide, potassium hydroxide, magnesium hydroxide or calcium hydroxide.

The starting compounds of the formulas II-b and II-c can be prepared by Method C.

METHOD C

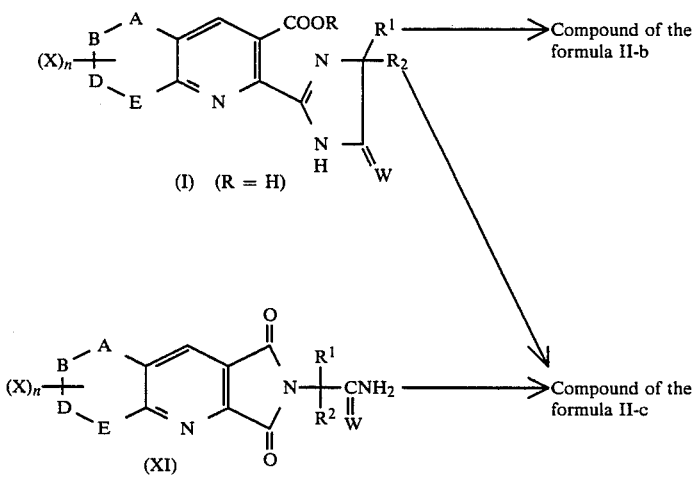

wherein A, B, D, E, X, W, n, R, $R^1$ and $R^2$ are as defined above.

Namely, a compound of the formula I wherein R is a hydrogen atom is treated with a dehydrating condensation agent such as dicyclohexyl carbodiimide or acetic anhydride in a suitable solvent (such as dichloroethane, dichloromethane, tetrahydrofuran or acetic acid) to obtain a compound of the formula II-b or II-c.

Otherwise, a compound of the formula XI is treated with an alkali metal hydride such as sodium hydride or with a base such as DBU (1,8-diazabicyclo[5,4,0]-7-undecene) in an aromatic hydrocarbon solvent such as benzene, toluene or xylene, to obtain a compound of the formula II-c.

REACTION SCHEME 4

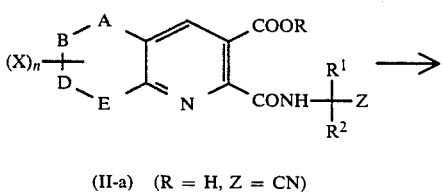

(II-a)  (R = H, Z = CN)

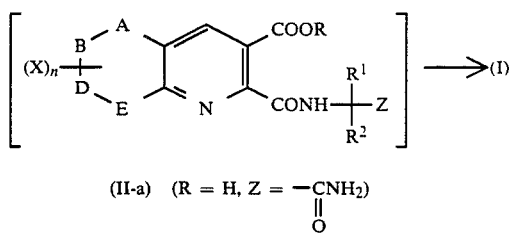

(II-a)  (R = H, Z = —CNH$_2$)
              ‖
              O wherein A, B, D, E, X, W, Z, n, R, $R^1$ and $R^2$ are as defined above.

Namely, a compound of the formula II-a wherein R is a hydrogen atom and Z is CN, is reacted with from 2 to 10 equivalent mols of an alkali metal hydroxide such as sodium hydroxide or potassium hydroxide in water with an aprotic polar solvent such as dimethylsulfoxide or in an aqueous solution of a $C_1$–$C_4$ alcohol at a temperature of from 25° to 110° C., if necessary, with an addition of from 2 to 5 equivalent mols of an aqueous hydrogen peroxide solution having a concentration of from 30 to 90%, and then, the reaction mixture is acidified with a mineral acid such as hydrochloric acid or sulfuric acid to obtain a compound of the formula I wherein R is a hydrogen atom and W is an oxygen atom.

Further, as described with respect to Reaction Scheme 1, the compound of the formula I wherein R is a hydrogen atom can be converted to compound of the formula I having various R other than a hydrogen atom, by esterification, by ester exchange or by neutralization with ammonia, an organic amine such as isopropylamine, an alkali metal or alkaline earth metal hydroxide such as sodium hydroxide, potassium hydroxide, magnesium hydroxide or calcium hydroxide.

In a similar manner, a compound of the formula II-a wherein R is an alkali metal ion, an alkaline earth metal ion, an ammonium ion or a quaternary ammonium ion, can be cyclized directly to obtain the corresponding compound of the formula I.

The starting compound of the formula II-a wherein R is a hydrogen atom and Z is CN, can be prepared by the following Method D.

METHOD D

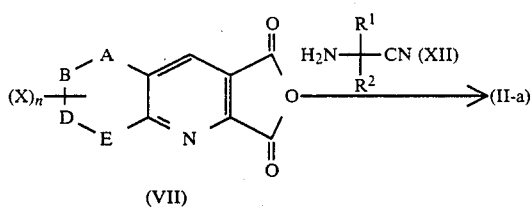

wherein R is a hydrogen atom, Z is a nitrile group, W is an oxygen atom, and A, B, D, E, X, n, $R^1$ and $R^2$ are as defined above.

Namely, a compound of the formula VII and a compound of the formula XII are reacted in a suitable solvent, preferably in diethyl ether, tetrahydrofuran, dimethoxyethane, acetonitrile or a low boiling halogenated hydrocarbon, in an inert gas stream at a temperature of from 20° to 60° C., to obtain a compound of the formula II-a wherein R is a hydrogen atom and Z is CN. Sometimes, an isomer carboxylic acid amide derivative of the formula II-a' may be produced as a by-product.

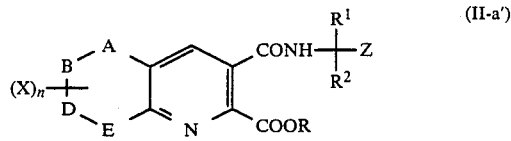

wherein R is a hydrogen atom, Z is a nitrile group, and A, B, D, E, X, n, $R^1$ and $R^2$ are as defined above.

The intermediate compounds of the formulas II-a, II-a', II-b, II-c, V, VI, VII, IX, IX, X and XI to be used in the present invention are novel compounds.

The compounds of the formula I of the present invention can be prepared by either one of the abovementioned Reaction Schemes 1, 2, 3 and 4. The preparation will be specifically described in the following Synthetic Examples.

SYNTHETIC EXAMPLE 1

Preparation of

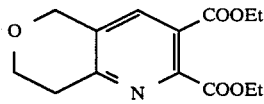

4.6 g (0.046 mol) of tetrahydro-4H-pyran-4-one and 3.3 g (0.047 mol) of pyrrolidine were heated and refluxed in 130 ml of benzene for 5 hours by an aid of a Dean-Stark trap, and then cooled, and the solvent was distilled off to obtain an oily substance (enamine product). Then, 70 ml of ethanol was added thereto, and 13 g (0.053 mol) of ethyl ethoxymethyleneoxaloacetate was dropwise added thereto. The mixture was stirred at room temperature for 1 hour. Then, 9 g (0.117 mol) of ammonium acetate was added thereto, and the mixture was refluxed under heating for 1 hour. After cooling the mixture, the solvent was distilled off, and the residue was extracted with chloroform. The extract was washed with water, and dried over anhydrous sodium sulfate. The solvent was distilled off to obtain a crude product of the above identified compound. The crude product was purified by column chromatography to obtain 5.28 g (yield: 43%) of the above identified compound.

Pale yellow liquid, refractive index $n_D^{25} = 1.5162$.

NMR (δ value (CDCl$_3$)): 1.37 (t, 3H), 1.40 (t, 3H), 3.00–3.18 (m, 2H), 3.97–4.16 (m, 2H), 4.35 (q, 2H), 4.44 (q, 2H), 4.80 (bs, 2H), 7.82 (s, 1H).

SYNTHETIC EXAMPLE 2

Preparation of

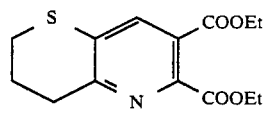

5.0 g (0.043 mol) of tetrahydrothiopyran-3-one, 3.7 g (0.044 mol) of pyrrolidine and 0.4 g of p-toluene sulfonic acid were heated and refluxed in 190 ml of benzene for 6 hours by an aid of a Dean-Stark trap, and then cooled. The solvent was distilled off to obtain an oily enamine product. Then, 70 ml of ethanol was added thereto, and 12 g (0.049 mol) of ethyl ethoxymethyleneoxaloacetate was dropwise added thereto. The mixture was stirred at room temperature for 1 hour. Further, 6.6 g (0.086 mol) of ammonium acetate was added thereto, and the mixture was refluxed under heating for 2 hours. After cooling the mixture, the solvent was distilled off. The reaction mixture was extracted with chloroform, and the extract was washed with water, and dried over anhydrous sodium sulfate. The solvent was distilled off to obtain a crude product of the above identified compound. The crude product was purified by column chromatography to obtain 8.1 g (yield: 63%) of the diester product.

Pale yellow liquid, refractive index $n_D^{25} = 1.5532$.

NMR (δ value (CDCl$_3$)): 1.38 (t, 3H), 1.41 (t, 3H), 2.10–2.45 (m, 2H), 2.98–3.18 (m, 4H), 4.35 (q, 2H), 4.45 (q, 2H), 7.83 (s, 1H).

SYNTHETIC EXAMPLE 3

Preparation of

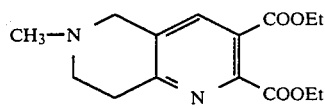

12 g (0.11 mol) of 1-methyl-4-piperidone and 9.1 g (0.13 mol) of pyrrolidine were heated and refluxed in 100 ml of benzene for 3 hours by an aid of a Dean-Stark trap, and then cooled. The solvent was distilled off to obtain an oily enamine product. Then, 100 ml of ethanol was added thereto, and 26 g (0.11 mol) of ethyl ethoxymethyleneoxaloacetate was dropwise added thereto. The mixture was stirred at room temperature for 1 hour. Further, 17 g (0.22 mol) of ammonium acetate was added thereto, and the mixture was refluxed under heating for 1 hour. After cooling the mixture, the solvent was distilled off. The reaction mixture was extracted with chloroform, and the extract was washed with water and dried over anhydrous sodium sulfate. The solvent was distilled off to obtain a crude product, which was then purified by column chromatography to obtain 4.0 g (yield: 13%) of the above identified compound.

Pale yellow liquid, refractive index $n_D^{25} = 1.5246$.

NMR (δ value (CDCl₃)): 1.37 (t, 3H), 1.40 (t, 3H), 2.48 (s, 3H), 2.70–2.90 (m, 2H), 3.05–3.25 (m, 2H), 3.63 (s, 2H), 4.35 (q, 2H), 4.45 (q, 2H), 7.84 (s, 1H).

SYNTHETIC EXAMPLE 4

Preparation of

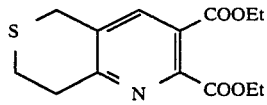

5.2 g (0.045 mol) of tetrahydrothiopyran-4-one and 3.5 g (0.049 mol) of pyrrolidine were heated and refluxed in 170 ml of benzene for 4 hours by an aid of a Dean Stark trap. After cooling the mixture, the solvent was distilled off to obtain an oily enamine product. 50 ml of ethanol was added thereto, and 12 g (0.049 mol) of ethyl ethoxymethyleneoxaloacetate was dropwise added thereto. The mixture was stirred at room temperature for 2 hours. Further, 8 g (0.010 mol) of ammonium acetate was added thereto, and the mixture was refluxed under heating for 2 hours. After cooling the mixture, the solvent was distilled off, and the mixture was extracted with chloroform. The extract was washed with water and dried over anhydrous sodium sulfate. The solvent was distilled off to obtain a crude product, which was then purified by column chromatography to obtain 8.4 g (yield: 67%) of the above identified compound.

Pale yellow liquid, refractive index $n_D^{25} = 1.5478$.

NMR (δ value (CDCl₃)): 1.36 (t, 3H), 1.39 (t, 3H), 2.87–3.07 (m, 2H), 3.18–3.40 (m, 2H), 3.82 (s, 2H), 4.35 (q, 2H), 4.45 (q, 2H), 7.90 (s, 1H).

SYNTHETIC EXAMPLE 5

Preparation of

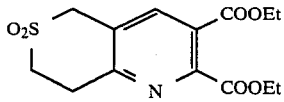

2.5 g (0.085 mol) of diethyl dihydrothiopyrano[4,3-b]pyridinedicarboxylate was dissolved in 30 ml of acetic acid, and 1.8 g of an aqueous hydrogen peroxide solution (35%) was added. The mixture was stirred at room temperature overnight. Then, water was added, and the mixture was extracted with chloroform. The extract was washed with water and then dried. The solvent was distilled off to obtain a crude product, which was then purified by column chromatography to obtain 2.55 g (yield: 92%) of the above identified S,S-dioxide product.

Pale yellow crystal, m.p.: 154°–157° C.

SYNTHETIC EXAMPLE 6

Preparation of

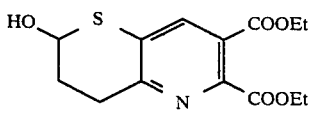

3.0 g (0.01 mol) of the diester product prepared in Synthetic Example 2 was dissolved in 15 ml of acetic acid, and 1.1 g of an aqueous hydrogen peroxide solution (35%) was added thereto. The mixture was stirred at room temperature overnight. Then, water was added, and the mixture was extracted with chloroform. The extract was washed with water, and then dried. The solvent was distilled off to obtain a crude product of the S-oxide. The S-oxide was dissolved in 100 ml of acetic anhydride, and heated and stirred at 130° C. for 6 hours. The solvent was distilled off, and the residual oily substance was purified by column chromatography to obtain 2.4 g (yield: 67%) of the Pummerer rearrangement product i.e. 2-acetoxy product.

NMR (δ value (CDCl₃)): 1.36 (t, 3H), 1.40 (t, 3H), 2.10 (s, 3H), 2.2–2.5 (m, 2H), 3.1–3.3 (m, 2H), 4.32 (q, 2H), 4.42 (q, 2H), 6.17 (t, 1H), 7.82 (s, 1H).

2.4 g (0.068 mol) of the 2-acetoxy product was dissolved in 8 ml of chloroform, and added to 8 ml of a chloroform solution containing a stoichiometric amount of sodium ethoxide. The mixture was stirred at room temperature for 5 hours. Then, water was added thereto, and the mixture was weakly acidified with acetic acid and extracted with chloroform. The extract was dried. The solvent was distilled off, and the residue was purified by column chromatography to obtain 1.4 g (yield: 66%) of the above identified compound.

SYNTHETIC EXAMPLE 7

Preparation of

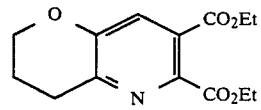

5.2 g (52 mmol) of tetrahydropyran-3-one and 4.25 g (59 mmol) of pyrrolidine were heated and refluxed in 100 ml of benzene for 3 hours by an aid of a Dean Stark trap. The solvent was distilled off under reduced pressure, whereby the presence of two types of enamine products was confirmed by NMR. 7.7 g (50 mmol) of the enamine products were dissolved in 150 ml of anhydrous ethanol, and 15.2 g (62 mmol) of ethyl ethoxymethylene oxaloacetate was dropwise added thereto. The mixture was stirred at room temperature for 2 hours. Then, 14.8 g (0.21 mol) of ammonium acetate was added thereto. The mixture was refluxed under heating and stirring for 1 hour. After cooling the mixture, the solvent was distilled off. The mixture was extracted with ethyl acetate, and the extract was dried. The solvent was distilled off under reduced pressure, and the residue was purified by column chromatography to obtain 3.3 g of a mixture of the above identified diester product and its isomer. From the NMR analysis, the ratio was found to be 2:1.

NMR (δ value (CDCl₃)) of the above identified compound

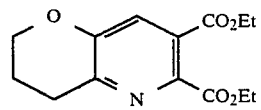

1.37 (t, 3H), 1.39 (t, 3H), 2.21 (dd, 2H), 3.04 (t, 2H), 4.2–4.5 (m, 2H), 4.30 (q, 2H), 4.35 (q, 2H), 7.45 (s, 1H).

NMR (δ value (CDCl₃)) of the isomer

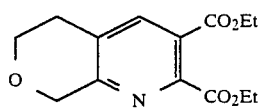

1.38 (t, 3H), 1.40 (t, 3H), 2.97 (t, 2H), 4.0 (t, 2H), 4.37 (q, 2H), 4.42 (q, 2H), 4.82 (s, 2H), 7.95 (s, 1H).

SYNTHETIC EXAMPLE 8

Preparation of

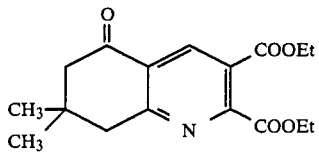

5.6 g (0.04 mol) of 1-amino-5,5-dimethyl-1-cyclohexen-3-one and 9.8 g (0.04 mol) of ethyl ethoxymethyleneoxaloacetate were dissolved in 100 ml of acetic acid, and the solution was stirred at room temperature for 12 hours. Acetic acid was distilled off under reduced pressure from the reaction solution, and then a saturated sodium hydrogencarbonate aqueous solution was added to the residue. The mixture was extracted with diethyl ether, and the extract was washed with water and dried. Then, the solvent was distilled off to obtain a crude product of the above identified compound, which was then purified by column chromatography to obtain 11.2 g (0.035 mol) (yield: 88%) of the above identified compound.

Pale yellow liquid, refractive index $n_D^{20.5} = 1.5172$.

NMR (δ value (CDCl$_3$)): 1.12 (s, 6H), 1.37 (t, J=6 Hz, 3H), 1.40 (t, J=6 Hz, 3H), 2.06(s, 2H), 3.08 (s, 2H), 4.35 (q, J=6 Hz, 2H), 4.44 (q, J=6 Hz, 2H), 8.69 (s, 1H).

SYNTHETIC EXAMPLE 9

Preparation of

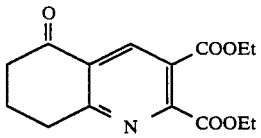

5.0 g (0.045 mol) of 1-amino-1-cyclohexen-3-one and 11.0 g (0.045 mol) of ethyl ethoxymethyleneoxaloacetate were dissolved in 100 ml of acetic acid. The solution was stirred at room temperature for 5 hours, then heated to 100° C. and reacted for further 1 hour.

Acetic acid was distilled off from the reaction solution under reduced pressure, and then a saturated sodium hydrogencarbonate aqueous solution was added to the residue. The mixture was extracted with diethyl ether, and the organic layer was washed with water and dried. Then, the solvent was distilled off to obtain a crude product of the above identified compound. The crude product was purified by column chromatography to obtain 11.6 g (0.040 mol) (yield: 89%) of the above identified compound.

Pale yellow liquid, refractive index $n_D^{20.5} = 1.5180$.

NMR (δ value (CDCl$_3$)): 1.37 (t, J=6.5 Hz, 3H), 1.37 (t, J=6.5 Hz, 3H), 2.25 (m, 2H), 2.74 (m, 2H), 3.22 (m, 2H), 4.36 (q, J=6.5 Hz, 2H), 4.44 (q, J=6.5 Hz, 2H), 8.71 (s, 1H).

SYNTHETIC EXAMPLE 10

Preparation of

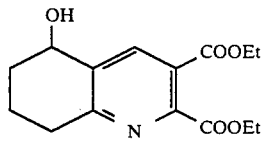

1.0 g of sodium borohydride was added to 100 ml of methanol solution of 6.0 g of the pyridine dicarboxylic acid diester prepared in Synthetic Example 9. The mixture was stirred at room temperature for 3 hours. Then, dilute hydrochloric acid was added to the reaction solution, and the mixture was extracted with diethyl ether. The organic layer was washed with water and dried. Then, the solvent was distilled off to obtain 6.0 g of the above identified compound.

Colorless transparent liquid, refractive index $n_D^{20} = 1.5308$.

NMR (δ value (CDCl$_3$)): 1.34 (t, HJ=6.5 Hz), 1.37 (t, J=6.5 Hz), 1.96 (m), 2.95 (m), 4.29 (q, J=6.5 Hz), 4.38 (q, J=6.5 Hz), 4.79 (bs), 8.27 (s).

SYNTHETIC EXAMPLE 11

Preparation of

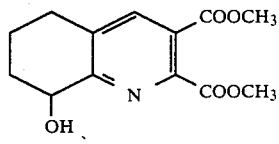

(a) A mixture comprising 2.8 g of diethyl 5,6,7,8-tetrahydroquinoline-2,3-dicarboxylate, 10 ml of acetic acid and 1.1 ml of a 35% hydrogen peroxide aqueous solution, was stirred at 75° C. for 3 hours under heating. 1.0 ml of a 35% hydrogen peroxide aqueous solution was added thereto, and the mixture was further reacted at 75° C. for 9 hours. After cooling the mixture, water was added thereto, and the mixture was extracted with chloroform. The organic layer was dried, and then the solvent was distilled off to obtain an oily substance. This oily substance was added to 50 ml of acetic anhydride under reflux, and refluxed for 15 minutes. The solvent was distilled off under reduced pressure. Water was added to the residue, and the mixture was extracted with diethyl ether. The organic layer was dried, and then the solvent was distilled off. The residue was purified by column chromatography to obtain 2.3 g (yield: 69%) of diethyl 8-acetoxy-5,6,7,8-tetrahydroquinoline-2,3-dicarboxylate.

NMR (δ value (CDCl$_3$)): 1.35 (t, J=7.0 Hz, 3H), 1.39 (t, J=7.0 Hz, 3H), 2.08 (s, 3H), 2.10 (m, 4H), 2.85 (m, 2H), 4.35 (q, J=7.0 Hz, 2H), 4.41 (q, J=7.0 Hz, 2H), 5.92 (m, 1H), 7.79 (s, 1H).

(b) 3.0 g of the acetate prepared in step (a), 2.2 g of sodium hydroxide, 30 ml of methanol and 30 ml of water, were stirred at room temperature for one day and night, and then acidified with hydrochloric acid, and then evaporated under reduced pressure to dryness. To the residue, 60 ml of methanol and 2.0 ml of concentrated sulfuric acid were added, and the mixture was refluxed under heating for 4 hours. The reaction solution was poured into ice water, and extracted with chloroform. The organic layer was dried, and then the solvent was distilled off to obtain the above identified compound.

Pale yellow crystal, m.p.: 58°–64° C.

NMR (δ value (CDCl₃)): 2.00 (m, 4H), 2.87 (m, 2H), 2.89 (s, 3H), 3.96 (s, 3H), 4.71 (m, 1H), 7.87 (s, 1H).

SYNTHETIC EXAMPLE 12

Preparation of

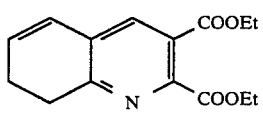

(1) 3 g of p-toluene sulfonic acid was added to a xylene solution containing 10 g of the pyridine dicarboxylic acid diester prepared in Synthetic Example 10, and the mixture was refluxed under heating in a helium atmosphere while dehydrating by an aid of a Dean Stark. After cooling the mixture, the mixture was extracted with ethyl ether. The organic layer was washed with an aqueous sodium carbonate solution and then with dilute hydrochloric acid, and dried. Then, the solvent was distilled off to obtain 8.6 g of a crude product of the above identified compound. The crude product was purified by column chromatography to obtain 6.9 g of the above identified compound.

Pale yellow liquid, refractive index $n_D^{20} = 1.5447$.

NMR (δ value (CDCl₃)): 1.37 (t, J=7.25 Hz, 3H), 1.41 (t, J=7.25 Hz, 3H), 2.55 (m, 2H), 3.04 (d, J=9.25 Hz, 2H), 4.37 (q, J=7.25 Hz, 2H), 4.45 (q, J=7.25 Hz, 2H), 6.15–6.53 (m, 2H), 7.72 (s, 1H).

(2) To a 200 ml of diethyl ether solution containing 7 g (0.024 mol) of the pyridine dicarboxylic acid diester prepared in Synthetic Example 10 and 3.8 g of pyridine, 5.5 g of methylchlorosulfinate was dropwise added under cooling with ice, and the mixture was stirred for 1 hour. Water was added to the reaction solution, and the mixture was extracted with diethyl ether. The organic layer was separated and dried. Then, the solvent was distilled off under reduced pressure to obtain an oily substance.

NMR (δ value (CDCl₃)): 1.35 (t, J=7.0 Hz, 3H), 1.40 (t, J=7.0 Hz, 3H), 2.10 (m, 4H), 3.02 (m, 2H), 3.68 (s, 3H), 4.36 (t, J=7.0 Hz, 2H), 4.45 (t, J=7 Hz, 2H), 5.70 (m, 1H), 8.79 (s, 1H).

This oily substance was stirred at 150° C. for 1 hour. After cooling the reaction mixture, water was added thereto, and the mixture was extracted with diethyl ether. The organic layer was washed with an aqueous sodium carbonate solution, and dried. Then, the solvent was distilled off under reduced pressure to obtain a crude product of the above identified compound. The crude product was purified by column chromatography to obtain 2.7 g of the above identified compound.

SYNTHETIC EXAMPLE 13

Preparation of

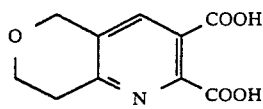

2.5 g (9.4 mmol) of diethyl dihydropyrano[4,3-]pyridine dicarboxylate prepared in Synthetic Example 1 was added to a solution mixture comprising 30 ml of ethanol and 30 ml of water with 0.9 g of sodium hydroxide dissolved therein, and the mixture was refluxed under heating for 2 hours. The mixture was cooled and acidified with hydrochloric acid, and the solvent was distilled off. The crude product was dissolved in ethanol and dried. The solvent was distilled to obtain 2.0 g (yield: 95%) of the above identified dicarboxylic acid.

Brown solid, m.p.: 153°–155° C. (decomposed).

NMR (δ value (DMSO-d₆)): 2.85–3.05 (m, 2H), 3.89–4.10 (m, 2H), 4.76 (s, 2H), 7.93 (s, 1H), 8.88 (s, 2H).

SYNTHETIC EXAMPLE 14

Preparation of

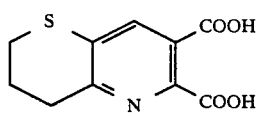

2.8 g (9.4 mmol) of diethyl dihydrothiopyrano[3,2-b]pyridine dicarboxylate prepared in Synthetic Example 2 was added to a solution mixture comprising 50 ml of ethanol and 50 ml of water with 0.9 g of sodium hydroxide dissolved therein, and the mixture was refluxed under heating for 2 hours. After cooling the mixture, the solvent was distilled off. The precipitated solid was dissolved in water and acidified with hydrochloric acid, whereby crystals precipitate. The crystals were collected by filtration and dried to obtain 1.5 g (yield: 67%) of the above identified dicarboxylic acid.

Brown crystal, m.p.: 190°–192° C. (decomposed).

NMR (δ value (DMSO-d₆)): 2.10–2.40 (m, 2H9, 2.90–3.20 (m, 4H9, 7.78 (s, 1H), 9.60–10.60 (b, 2H).

SYNTHETIC EXAMPLE 15

Preparation of

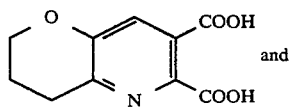

and

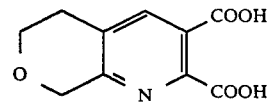

3.2 g (11.4 mmol) of the mixture of two types of diesters obtained in Synthetic Example 7 was added to a solution mixture comprising 2 ml of water and 30 ml of ethanol with 1.8 g (85%, 27.5 mmol) of potassium hydroxide dissolved therein, and the mixture was stirred at 60° C. for 2 hours. After cooling, the mixture was concentrated under reduced pressure. After an addition of water, the insoluble substances were filtered off. The filtrate was acidified with hydrochloric acid, whereby crystals precipitated. The crystals were collected by filtration and dried to obtain 1.8 g of a mixture of the above identified dicarboxylic acids. From the NMR analysis, the ratio was 3:2.

NMR of

[structure: bicyclic with O in ring, pyridine with two COOH groups]

(δ value (DMSO-d$_6$)) 2.11 (dd, 2H), 2.95 (t, 2H), 4.22 (t, 2H), 7.37 (s, 1H), 9.2-10.1 (b, 2H).

NMR of

[structure: bicyclic with O in ring, pyridine with two COOH groups]

(δ value (DMSO-d$_6$)) 2.97 (t, 2H), 3.93 (t, 2H), 4.70 (s, 2H), 7.93 (s, 1H), 9.2-10.1 (b, 2H).

SYNTHETIC EXAMPLE 16

Preparation of

[structure: tetrahydroquinoline dicarboxylic acid]

A mixture comprising 2.5 g (0.0091 mol) of diethyl pyridine dicarboxylate prepared in Synthetic Example 12, 1.5 g of potassium hydroxide, 2 ml of water and 30 ml of ethanol, was stirred at 60° C. for 1 hour. After cooling the mixture, anhydrous acetone was added. Precipitated crystals were collected by filtration, dried and again suspended in anhydrous acetone. The mixture was acidified with concentrated hydrochloric acid, and the precipitated crystals were collected by filtration. Further, the crystals were dissolved in ethanol, and insoluble substances were filtered off. Then, the organic layer was concentrated under reduced pressure to obtain 1.5 g (yield: 75%) of the above identified compound.

White crystal, m.p.: 168°-174° C. (decomposed).

NMR (δ value (DMSO-d$_6$)): 2.60 (m, 2H), 3.00 (d, J=8 Hz, 2H), 6.00-6.55 (m, 2H), 7.73 (s, 1H).

SYNTHETIC EXAMPLE 17

Preparation of

[structure: dimethyl-tetrahydroquinoline dicarboxylic acid with CH$_3$, CH$_3$ groups]

To 100 ml of a methanol solution containing 9.6 g of the pyridine dicarboxylic acid diester prepared in Synthetic Example 8, 2.2 g of sodium borohydride was added, and the mixture was stirred at room temperature for 3 hours. Then, dilute hydrochloric acid was added to the reaction solution, and the mixture was extracted with diether ether. The organic layer was washed with water and dried. Then, the solvent was distilled off to obtain 8.9 g (yield: 92%) of the reduced product. A solution comprising 3.0 g of this reduced product, 16 ml of acetic acid and 4 ml of concentrated sulfuric acid, was gradually heated from room temperature to the refluxing temperature, and the stirring was continued for 4 hours. After cooling, the reaction solution, water was added thereto, and the mixture was extracted with chloroform. The organic layer was washed with water and dried. Then, the solvent was distilled off to obtain 1.6 g (yield: 80%) of the above identified compound.

White crystal, m.p.: 175°-178° C. (decomposed).

NMR (δ value (DMSO-d$_6$): 1.08 (s, 6H), 2.86 (s, 2H), 5.91 (d, J=9.6 Hz, 1H), 6.39 (d, J=9.6 Hz, 1H), 7.75 (s, 1H), 11.90 (bs, 2H).

SYNTHETIC EXAMPLE 18

Preparation of

[structure: dimethyl-oxo-tetrahydroquinoline dicarboxylic acid with CH$_3$, CH$_3$ groups and C=O]

5.0 g of the pyridine dicarboxylic acid diester prepared in Synthetic Example 8 was added to a solution mixture comprising 30 ml of methanol, 30 ml of water and 1.7 g of sodium hydroxide, and the mixture was stirred at room temperature for 12 hours. Then, the solvent was distilled off under reduced pressure until the reaction solution became about ⅓. Then, 60 ml of water was added thereto, and the solution was acidified with an addition of concentrated hydrochloric acid, and extracted with chloroform. The organic layer was washed with water and dried. Then, the solvent was distilled off to obtain 3.1 g (yield: 93%) of the above identified compound.

White crystal, m.p.: 160°-162° C.

NMR (δ value (DMSO-d$_6$)): 1.04 (s, 6H), 2.62 (s, 2H), 3.06 (s, 2H), 8.54 (s, 1H), 12.20 (bs, 2H).

SYNTHETIC EXAMPLE 19

Preparation of

[structure: oxo-tetrahydroquinoline dicarboxylic acid with C=O]

6.6 g of the pyridine dicarboxylic acid diester prepared in Synthetic Example 9 was added to a solution mixture comprising 45 ml of methanol, 45 ml of water and 2.6 of sodium hydroxide. The mixture was refluxed for 2.5 hours, and the solvent was distilled off under reduced pressure. The residue was dissolved in water and acidified with concentrated hydrochloric acid, whereby white crystals precipitated. The white crystals were collected by filtration and dried to obtain 5.0 g (yield: 94%) of the above identified dicarboxylic acid.

White crystal, m.p.: 105°-1140° C.

NMR (δ value (DMSO-d$_6$)) 2.12 (m, 2H), 2.65 (m, 2H), 3.15 (m, 2H), 8.56 (s, 1H), 12.90 (bs, 2H).

SYNTHETIC EXAMPLE 20

Preparation of

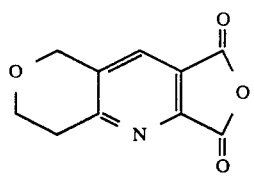

To an anhydrous ethanol solution containing 14.5 g (0.052 mol) of the diethyl ester product prepared in Synthetic Example 1, 5 ml of an aqueous solution containing 8.2 g (85%, 0.12 mol) of potassium hydroxide was added. The mixture was stirred at 60° C. for 2 hours. After cooling the mixture, acetone was added thereto, and the precipitates were collected by filtration, dried and suspended in acetone. The suspension was adjusted to pH 2 with concentrated hydrochloric acid. The isolated solid was 15.3 g of the corresponding dicarboxylic acid containing potassium chloride. 5 g of the solid was suspended in a solution mixture comprising 60 ml of acetic anhydride and 2.5 g of anhydrous sodium acetate, and the suspension was stirred at 60° C. for 1 hour. Then, the mixture was cooled and concentrated under reduced pressure. Chloroform and water were added thereto. The organic layer was separated, dried and concentrated, whereby 1.6 g of the above identified acid anhydride was isolated.

Light brown crystal, m.p.: 137°–141° C. (decomposed).

SYNTHETIC EXAMPLE 21

Preparation of

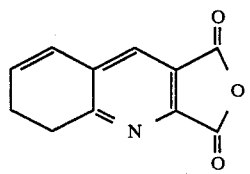

1.7 g of the pyridine dicarboxylic acid prepared in Synthetic Example 16, 2.0 g of sodium acetate and 25 ml of acetic anhydride were stirred at a temperature of 70° C. for 3 hours. The solvent was distilled off under reduced pressure, and water was added to the residue. The mixture was extracted with chloroform. The organic layer was washed with water, and dried. Then, the solvent was distilled off to obtain 1.4 g (yield: 90%) of the above identified dicarboxylic acid anhydride.

White crystal, m.p.: 145°–150° C. (decomposed).

NMR ($\delta$ value, (CDCl$_3$)): 2.73 (m, 2H), 3.24 (d, 2H), 6.55 (m, 2H), 7.78 (s, 1H).

SYNTHETIC EXAMPLE 22

Preparation of

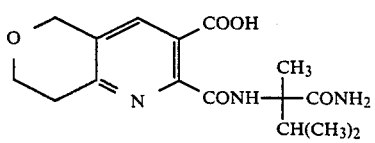

1.0 g (4.8 mmol) of the acid anhydride prepared in Synthetic Example 20 was dissolved in 30 ml of acetonitrile, and 0.67 g (5.1 mmol) of 2-amino-2,3-dimethylbutaneamide was added. The mixture was stirred at room temperature overnight. The solvent was distilled off under reduced pressure, and the residue was washed with diethyl ether, whereby the above identified amide was quantitatively obtained.

White crystal, m.p.: 140°–150° C. (decomposed).

SYNTHETIC EXAMPLE 23

Preparation of

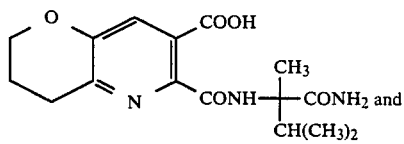

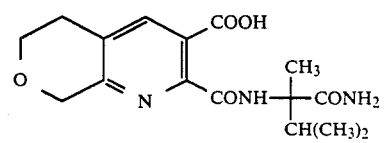

1.8 g (7.9 mmol) of a mixture of the two isomers of the pyridine dicarboxilic acid prepared in Synthetic Example 15 was heated and stirred in 30 ml of acetic anhydride at 110° C. for 1 hour and 30 minutes. The mixture was cooled and concentrated under reduced pressure. Toluene was added to the residue, and the mixture was concentrated under reduced pressure to obtain 1.6 g of a mixture of the corresponding two types of two isomers of the pyridine dicarboxylic acid anhydride. The acid anhydride was dissolved in 60 ml of acetonitrile, and 1.1 g of 2-amino-2,3-dimethylbutaneamide was added thereto. The mixture was stirred at room temperature overnight. Then, the solvent was distilled off to obtain 2.7 g of a mixture of the above identified amide compounds.

Pale brown crystal, m.p.: 165°–173° C. (decomposed).

SYNTHETIC EXAMPLE 24

Preparation of

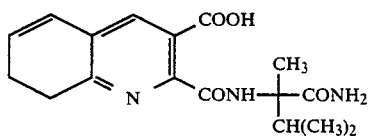

To 30 ml of an acetonitrile solution containing 1.0 g of the pyridine dicarboxylic acid anhydride prepared in Synthetic Example 21, 0.7 g of 2-amino-2,3-dimethylbutaneamide was added. The mixture was stirred at room temperature overnight. The precipitated crystals were collected by filtration, and washed with isopropyl ether, whereby the above identified compound was obtained quantitatively.

White crystal, m.p.: 125°–131° C. (decomposed).

SYNTHETIC EXAMPLE 25

Preparation of

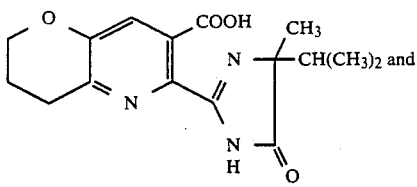

Compound No. 1

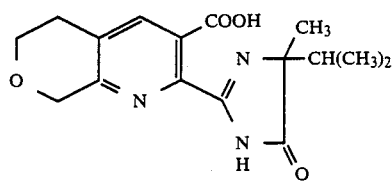

Compound No. 85

2.7 g (7.9 mmol) of the mixture of the two isomers prepared in Synthetic Example 23 was added to 30 ml of an aqueous solution containing 1.3 g of sodium hydroxide. The mixture was heated and stirred at 80° C. for 2 hour and 30 minutes. The reaction mixture was cooled, acidified by an addition of concentrated hydrochloric acid, and extracted with chloroform. The extract was dried, and solvent was distilled off. The residue was purified by column chromatrography, whereby 0.59 g (yield: 24%) of Compound No. 1 of the present invention and 0.18 g (yield: 7%) of Compound No. 85 of the present invention, were isolated respectively.

Compound No. 1 of the present invention, White crystal, m.p.: 201°–204° C.

NMR (δ value (CDCl₃)): 1.91 (d, 3H), 2.11 (d, 3H), 1.50 (s, 3H), 1.9–2.4 (m, 1H), 2.18 (dd, 2H), 3.02 (t, 2H), 4.32 (t, 2H), 8.23 (s, 1H), 9.5–10.5 (b, 2H).

Compound No. 85 of the present invention, White crystal, m.p: 155°–159° C.

NMR (δ value (CDCl₃)): 1.92 (d, 3H), 2.12 (d, 3H), 1.52 (s, 3H), 1.95–2.4 (m, 1H), 3.07 (t, 2H), 4.03 (t, 2H), 4.82 (s, 2H), 8.75 (s, 1H), 9.2–10.2 (b, 2H).

SYNTHETIC EXAMPLE 26

Preparation of

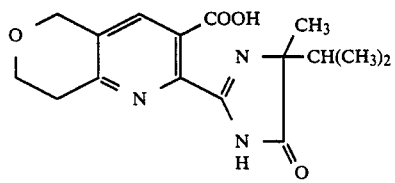

(Compound No. 2 of the present invention)

2.0 g (8.9 mmol) of the dicarboxylic acid prepared in Synthetic Example 13 was dissolved in 60 ml of acetic anhydride, and the solution was stirred under heating at 110° C. for 2 hours. The reaction solution was cooled and concentrated under reduced pressure to obtain a brown solid. By the NMR analysis, the solid was confirmed to be the dicarboxylic acid anhydride. This solid was dissolved in 15 ml of pyridine, and 1.4 g (10.8 mmol) of 2-amino-2,3-dimethylbutaneamide was added thereto. The mixture was stirred overnight at room temperature. The solvent was distilled off under reduced pressure to obtain a crude product of the corresponding compound of the formula II-a. To this crude product, a solution comprising 1.6 g of sodium hydroxide and 20 ml of water, was added. The mixture was stirred at 80° C. for 3 hours. The mixture was cooled, then acidified with concentrated hydrochloric acid, and extracted with chloroform. The organic layer was washed with water and dried. Then, the solvent was distilled off to obtain a crude product of the above identified compound, which was then purified by column chromatography to obtain 0.9 g (yield: 32%) of Compound No. 2 of the present invention.

White crystal, m.p.: 215°–217° C.

NMR (δ value (CDCl₃)): 0.96 (d, 3H), 1.14 (d, 3H), 1.52 (s, 3H), 1.98–2.45 (m, 1H), 2.99–3.20 (m, 2H), 4.02–4.21 (m, 2H), 4.88 (s, 2H), 8.62 (s, 1H), 9.50–10.50 (b, 2H).

SYNTHETIC EXAMPLE 27

Preparation of

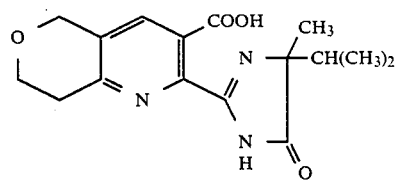

(Compound No. 2 of the present invention)

1.5 g (4.46 mmol) of the amide compound prepared in Synthetic Example 22 was added to 10 ml of an aqueous solution containing 0.8 g (93%, 18.6 mmol) of sodium hydroxide, and the mixture was stirred at 80° C. for 2 hours and 30 minutes. Then, the reaction mixture was cooled, then adjusted to pH 3 with hydrochloric acid, and extracted with chloroform. the extract was dried, and the solvent was distilled off. The residue was purified by column chromatography to obtain 0.34 g (yield: 24%) of Compound No. 2 of the present invention.

White crystal, m.p.: 215°–217° C.

NMR (δ value (CDCl₃)): 0.96 (d, 3H), 1.14 (d, 3H), 1.52 (s, 3H), 1.98–2.45 (m, 1H), 2.99–3.20 (m, 2H), 4.02–4.21 (m, 2H), 4.88 (s, 2H), 8.62 (s, 1H), 9.50–10.50 (b, 2H).

SYNTHETIC EXAMPLE 28

Preparation of

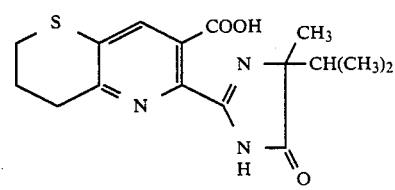

(Compound No. 15 of the present invention)

1.3 g (5.4 mmol) of the dicarboxylic acid obtained in Synthetic Example 14, was added to 80 ml of acetic anhydride, and the mixture was stirred under heating at 120° C. for 2 hours. After cooling the mixture, the solvent was distilled off to obtain the dicarboxylic acid anhydride. To this anhydride, 50 ml of acetonitrile and 0.75 g (5.8 mmol) of 2-amino-2,3-dimethylbutaneamide were added, and the mixture was stirred at room temperature overnight. The solvent was distilled off under reduced pressure to obtain 1.9 g of a crude product of the corresponding compound of the formula II-a. To this product, 0.95 g of sodium hydroxide and 20 ml of water were added. The mixture was stirred under heating at 80° C. for 3 hours. The mixture was cooled, then acidified with hydrochloric acid and extracted with chloroform. The organic layer was washed with water and dried. The solvent was distilled off under reduced pressure to obtain a crude product of the above identified compound. The crude product was purified by column chromatography to obtain 0.75 g (yield: 43%) of Compound No. 15 of the present invention.

White crystal, m.p.: 216°–217° C.

NMR (δ value (CDCl$_3$)): 0.90 (d, 3H), 2.12 (d, 3H), 2.52 (s, 3H), 2.03–2.35 (m, 1H), 2.20–2.45 (m, 2H), 2.97–3.22 (m, 4H), 8.62 (s, 1H), 9.50–10.50 (b, 2H).

SYNTHETIC EXAMPLE 29

Preparation of

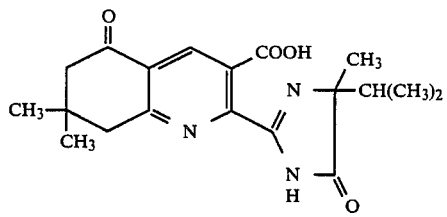

(Compound No. 7 of the present invention)

2.0 g of the pyridine dicarboxylic acid prepared in Synthetic Example 18, 1.6 g of trifluoroacetic anhydride and 20 ml of acetic anhydride were reacted at a temperature of from 50° to 80° C. for 3 hours, and the solvent was distilled under reduced pressure to obtain a crude product of the corresponding acid anhydride. To this crude product, 50 ml of acetonitrile and 1.2 g of 2-amino-2,3-dimethylbutaneamide were added, and the mixture was vigorously stirred at room temperature for one day and night. The solvent was distilled off under reduced pressure to obtain a crude product of the corresponding amide. To this crude product, 25 ml of water and 1.4 g of sodium hydroxide were added, and the mixture was stirred at 80° C. for 3 hours. The mixture was cooled, then acidified with a concentrated hydrochloric acid solution and extracted with chloroform. The organic layer was washed with water and dried. Then, the solvent was distilled off to obtain a crude product of the above identified compound. Then, the crude product was purified by column chromatography to obtain 1.3 g of Compound No. 7 of the present invention.

White crystal, m.p.: 213°–216° C. (decomposed).

NMR (δ value (CDCl$_3$)): 0.97 (d, J=6 Hz, 3H), 1.15 (d, J=6 Hz, 3H), 1.16 (s, 6H), 1.54 (s, 3H), 2.21 (qq, J=6 Hz, 1H), 2.65 (s, 2H), 3.14 (s, 2H), 9.31 (s, 1H).

SYNTHETIC EXAMPLE 30

Preparation of

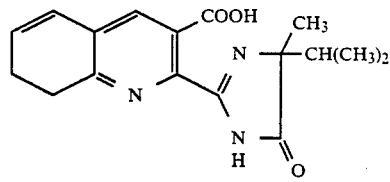

(Compound No. 3 of the present invention)

To 2.6 g of the amide prepared in Synthetic Example 24, 25 ml of water and 1.4 g of sodium hydroxide were added, and the mixture was stirred at 80° C. for 3 hours. After cooling the mixture, insoluble substances were removed. The mixture was acidified with an addition of acetic acid, whereby crystals precipitated. The crystals were collected by filtration and dried to obtain 0.8 g of white crystals of Compound No. 3 of the present invention.

White crystal, m.p.: 201.7°–206.3° C. (decomposed).

NMR (δ value (CDCl$_3$)): 0.95 (d, J=6 Hz, 3H), 1.14 (d, J=6 Hz, 3H), 1.58 (s, 3H), 2.19 (qq, J=6 Hz, 1H), 2.62 (m, 2H), 3.01 (m, 2H), 6.11–6.70 (m, 2H), 8.44 (s, 1H).

SYNTHETIC EXMAPLE 31

Preparation of

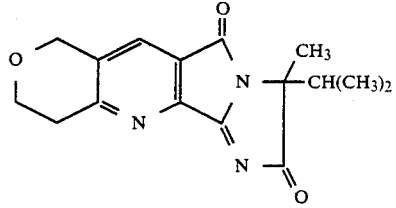

A mixture comprising 0.50 g (1.58 mmol) of Compound No. 2 of the present invention, 6 ml of acetic acid and 2 ml of acetic anhydride, was stirred under reflux for 5 hours. The mixture was cooled and concentrated under reduced pressure. Toluene was added to the residue, and the mixture was again concentrated under reduced pressure. The residual solid was formed into a slurry with isopropyl ether, then collected by filtration and dried to obtain 0.4 g (yield: 85%) of pale yellow crystals. From the nuclear magnetic resonance (NMR) and high performance liquid chromatography (HPLC) analyses of this substance, it was found that the desired 2,5-dione was about 80%, and the 3,5-dione was about 20%.

Pale yellow crystal, m.p.: 208°–218° C.

NMR (δ value (CDCl$_3$)):
0.95 (d, 3H), 1.11 (d, 3H), 1.66 (s, 3H), 2.0–2.6 (m, 1H), 3.27 (t, 2H), 4.12 (t, 2H), 4.91 (s, 2H), 7.78 (s, 1H).

SYNTHETIC EXAMPLE 32

Preparation of

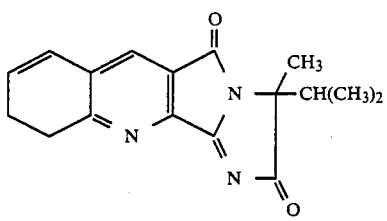

A mixture comprising 0.80 g (0.0026 mol) of Compound No. 3 of the present invention, 10 ml of acetic acid and 3 ml of acetic anhydride were stirred under reflux for 4 hours. The solvent was distilled off under reduced pressure. Toluene was added to the residue, and the solvent was again distilled off under reduced pressure. The precipitated crystals were washed a few times with hexane to obtain 0.70 g (yield: 91%) of crystals of the above identified compound. From the NMR and HPLC analyses, the crystals were found to comprise about 80% of the above identified compound and about 20% of the 3,5-dione isomer.

White crystal, m.p.: 110°–115° C.

NMR ($\delta$ value (CDCl$_3$)): 0.92 (d, J=7 Hz, 3H), 1.08 (d, J=7 Hz, 3H), 1.63 (s, 3H), 1.90–2.78 (m, 3H), 3.16 (d, J=8 Hz, 2H), 6.00–6.73 (m, 2H), 7.64 (s, 1H).

SYNTHETIC EXAMPLE 33

Preparation of

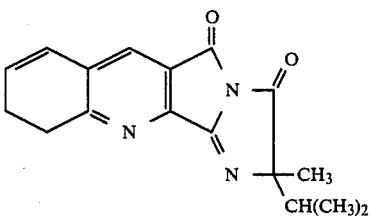

A mixture comprising 1.5 g (0.0047 mol) of Compound No. 3 of the present invention, 30 ml of methylene chloride and 1.07 g (0.005 mol) of dicyclohexylcarbodiimide, was stirred in a nitrogen atmosphere at room temperature for 24 hours. Then, the crystals were removed by filtration, and the organic layer was concentrated under reduced pressure to dryness. The crystals thereby obtained were purified by column chromatography to obtain 1.3 g (yield: 94%) of the above identified compound.

White crystals, m.p.: 188°–193°C.

NMR ($\delta$ value (CDCl$_3$)) 0.97 (d, J=7 Hz, 3H), 1.13 (d, J=7 Hz, 3H), 1.53 (s, 3H), 2.13 (m, 1H), 2.40–2.80 (m, 2H), 3.16 (d, J=8 Hz, 2H), 6.15–6.75 (m, 2H), 7.70 (s, 1H).

SYNTHETIC EXAMPLE 34

Preparation of

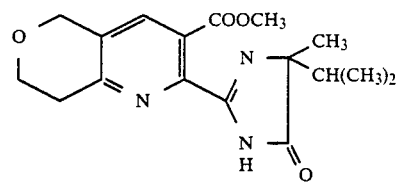

(Compound No. 73 of the present invention)

0.3 g (1.0 mmol) of the condensation product prepared in Synthetic Example 31 was added to a mixture of 50 ml of anhydrous methanol and 50 mg (50%, 1.0 mmol) of sodium hydride. The mixture was stirred at room temperature overnight. Acetic acid was added to weakly acidify the mixture, and then the mixture was concentrated under reduced pressure and extracted with chloroform. The extract was washed with water and dried. Chloroform was distilled off under reduced pressure, and the residue was purified by column chromatography to obtain 0.2 g of Compound No. 73 of the present invention.

White crystal, m.p.: 229°–233° C.

Synthetic Example 35

Preparation of

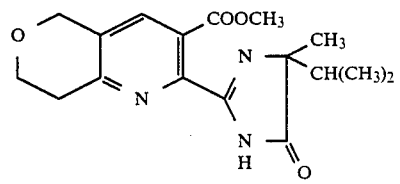

(Compound No. 73 of the present invention)

0.3 g (0.94 mmol) of the carboxylic acid prepared in Synthetic Example 25 was added to a solution containing 40 ml of anhydrous methanol and 0.3 ml of concentrated sulfuric acid. The mixture was refluxed under heating overnight. After cooling the mixture, methanol was distilled off. The mixture was extracted with chloroform, and the extract was washed with water, then dried and concentrated under reduced pressure. The residue was purified by column chromatography to isolate 0.18 g (yield: 58%) of the above identified methyl ester.

White crystal, m.p.: 229°–233° C.

NMR ($\delta$ value (CDCl$_3$)) 0.89 (d, 3H), 1.07 (d, 3H), 1.48 (s, 3H), 1.90–2.33 (m, 1H), 3.04 (t, 2H), 3.87 (s, 3H), 4.09 (t, 3H), 4.80 (s, 2H), 7.42 (s, 1H), 8.75 (b, 1H).

SYNTHETIC EXAMPLE 36

Preparation of

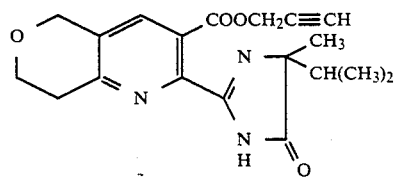

-continued (Compound No. 33 of the present invention)

(Compound No. 33 of the present invention)

0.21 g of sodium hydride (50%) was added to 20 ml of a tetrahydrofuran solution containing 0.15 g (2.7 mmol) of propargyl alcohol, and the mixture was stirred at room temperature for 1 hour. Then, 0.4 g (1.3 mmol) of the condensation product prepared in Synthetic Example 31 was added thereto, and the mixture was stirred at room temperature for 2 days. Acetic acid was added to weakly acidify the mixture, and the mixture was concentrated under reduced pressure and extracted with chloroform. The extract was washed with water and dried. The chloroform was distilled off, and the residue was purified by column chromatography to obtain 0.3 g of Compound No. 33 of the present invention.

White crystal, m.p.: 194°–199° C.

SYNTHETIC EXAMPLE 37

Preparation of

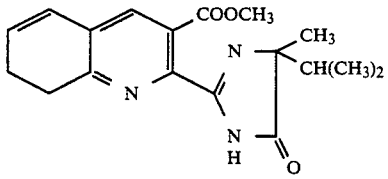

(Compound No. 69 of the present invention)

500 mg of the tetracyclic compound (2,5-dione) prepared in Synthetic Example 32 was added to a solution comprising 200 mg of sodium hydride (50%) and 20 ml of methanol, and the mixture was refluxed under heating for 1 hour. Then, the solvent was distilled off under reduced pressure. Chloroform was added to the residue, and organic layer was washed with water and dried. The solvent was distilled off under reduced pressure. The crude product thereby obtained was isolated by column chromatography to obtain 270 mg of Compound No. 69 of the present invention.

White crystal, m.p.: 158°–164° C.

NMR ($\delta$ value (CDCl$_3$)) 0.87 (d, J=7 Hz, 3H), 1.03 (d, J=7 Hz, 3H), 1.35 (s, 3H), 2.00 (m, 1H), 2.30–2.70 (m, 2H), 2.93 (d, J=7 Hz, 2H), 3.83 (s, 3H), 6.00–6.60 (m, 2H), 7.30 (s, 1H), 8.63 (bs, 1H).

SYNTHETIC EXAMPLE 38

Preparation of

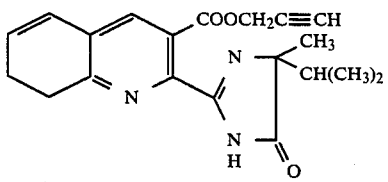

(Compound No. 87 of the present invention)

500 mg of the tetracyclic compound (3,5-dione) prepared in Synthetic Example 33, was added to a solution comprising 170 mg of 50% sodium hydride, 300 mg of propargyl alcohol and 20 ml of tetrahydrofuran, and the mixture was stirred at room temperature for 2 days. Acetic acid was added to weakly acidify the mixture. Then, the solvent was distilled off under reduced pressure. Chloroform was added to the residue, and the mixture was washed with water and dried. Then, the solvent was distilled off under reduced pressure. The crude product thereby obtained was purified by column chromatography to obtain 190 mg of Compound No. 87 of the present invention.

White crystal, m.p.: 169°–175° C.

NMR ($\delta$ value CDCl$_3$)): 0.87 (d, J=7 Hz, 3H), 1.05 (d, J=7 Hz, 3H), 1.35 (s, 3H), 2.00 (m, 1H), 2.35–2.73 (m, 2H), 2.51 (t, J=2 Hz, 1H), 2.96 (d, J=7 Hz, 2H), 4.84 (d, J=2 Hz, 2H), 6.02–6.64 (m, 2H), 7.29 (s, 1H), 8.99 (bs, 1H).

SYNTHETIC EXAMPLE 39

Preparation of

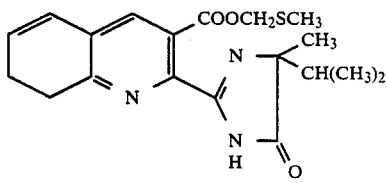

(Compound No. 72 of the present invention)

A mixture comprising 1.0 g (0.0032 mol) of the pyridine carboxylic acid (Compound No. 3 of the present invention) prepared in Synthetic Example 30, 4.7 g of tert-butyl bromide, 2.9 g of sodium hydrogencarbonate and 20 ml of dried dimethylsulfoxide, was stirred at room temperature for 60 hours. After the reaction, the reaction solution was poured into ice water, and extracted with ethyl ether. The ether solution was washed with water and dried over anhydrous sodium sulfate. Then, the ether was distilled off under reduced pressure. The residue was purified by column chromatography to obtain 0.60 g (yield: 50%) of Compound No. 72 of the present invnetion.

White crystal, m.p.: 198°–202° C.

NMR ($\delta$ value (CDCl$_3$)): 0.85 (d, J=7 Hz, 3H), 1.03 (d, J=7 Hz, 3H), 1.35 (s, 3H), 2.04 (qq, J=7 Hz, 1H), 2.25 (s, 3H), 2.54 (m, 2H), 2.93 (d, J=7 Hz, 2H), 5.27 (s, 2H), 5.95–6.54 (m, 2H), 7.30 (s, 1H), 8.93 (bs, 1H).

SYNTHETIC EXAMPLE 40

Preparation of

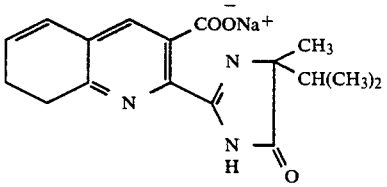

(Compound No. 80 of the present invention)

0.07 g of sodium hydroxide was dissolved in 20 ml of methanol, and then 0.50 g (0.0016 mol) of Compound No. 3 of the present invention was added thereto. The solvent was distilled off under reduced pressure to obtain a solid. This solid was dissolved in ethanol, and after an addition of ethyl ether, recrystallized to obtain 0.53 g of Compound No. 80 of the present invention.

White crystal, m.p.: 260° C. or higher.

NMR (δ value (D₂O)): 0.85 (d, J=7 Hz, 3H), 1.05 (d, J=7 Hz, 3H), 1.35 (s, 3H), 2.20 (qq, J=7 Hz, 1H), 2.30-2.67 (m, 2H), 2.88 (d, J=8 Hz, 2H), 5.95-6.64 (m, 2H), 7.49 (s, 1H).

SYNTHETIC EXAMPLE 41

Preparation of

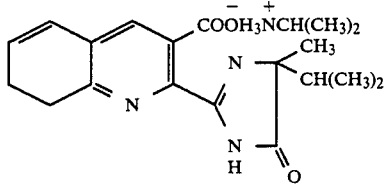

(Compound No. 13 of the present invention)

A mixture comprising 0.50 g (0.0016 mol) of Compound No. 3 of the present invention, 0.10 g of isopropylamine and 30 ml of methanol, was stirred at room temperature for 30 minutes, and then the solvent was distilled off under reduced pressure to obtain crude crystals of the above identified compound. The crude crystals were suspended in ethyl ether, and filtered to obtain 0.41 g (yield: 69%) of Compound No. 13 of the present invention.

White crystal, m.p.: 140°-205° C. (gradually decomposed).

NMR (δ value (CDCl₃)): 0.89 (d, J=7 Hz, 3H), 1.02 (d, J=7 Hz, 3H), 1.24 (d, J=6 Hz, 6H), 1.38 (s, 3H), 2.00 (qq, J=7 Hz, 1H, 2.22-2.70 (m, 2H), 2.90 (d, J=7 Hz, 2H), 3.39 (m, 1H), 5.85-6.55 (m, 2H), 7.48 (s, 1H), 7.88 (bs, 3H).

SYNTHETIC EXAMPLE 42

Preparation of

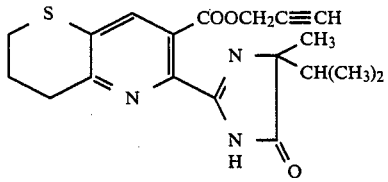

(Compound No. 74 of the present invention)

1.3 g (4.1 mmol) of the tetracyclic compound (the 3,5-dione) obtained from Compound No. 15 of the present invention by means of Synthetic Example 32, was added to 30 ml of tetrahydrofuran solution containing 0.2 g of 50% sodium hydride and 0.46 g of propargyl alcohol, and the mixture was stirred at room temperature overnight. The solvent was distilled off under reduced pressure, and the mixture was neutralized with acetic acid and extracted with chloroform. The extract was washed with water and dried. Then, the solvent was distilled off under reduced pressure. The crude product thereby obtained was isolated and purified by column chromatography to obtain 1.1 g of Compound No. 74 of the present invention.

White crystal, m.p.: 154°-156° C.

NMR (δ value (CDCl₃)): 0.87 (d, 3H), 2.04 (d, 3H), 2.86 (s, 3H), 1.85-2.24 (m, 1H), 2.05-2.43 (m, 2H), 2.50 (t, 1H), 2.86-3.20 (m, 4H), 4.83 (d, 2H), 7.45 (s, 1H), 8.72 (bs, 1H).

SYNTHETIC EXAMPLE 43

Preparation of

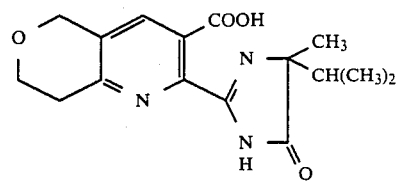

(Compound No. 2 of the present invention)

2.90 g of the dihydropyrano[4,3-b]pyridinedicarboxylic acid prepared in Synthetic Example 13, was dissolved in 60 ml of acetic anhydride, and the solution was stirred under heating at 80° C. for 2 hours. After cooling, the reaction solution was concentrated under reduced pressure to obtain a brown solid. This solid was dissolved in 50 ml of dichloromethane, and 1.46 g of a compound of the formula XII wherein $R^1$ is a methyl group and $R^2$ is an isopropyl group, was added. The mixture was stirred under reflux for 2 hours. The solvent was distilled off under reduced pressure to obtain a crude product (viscous substance) of a mixture comprising the corresponding compound of the formula II-a' and compound of the formula II-a'. This crude product was mixed with 1.69 g (0.042 mol) of sodium hydroxide and 11 ml of water, and the mixture was heated to 80° C. To this solution, 4.4 g (0.040 mol) of a 30% hydrogen peroxide aqueous solution was slowly added. After the addition of hydrogen peroxide, 1.0 g of sodium hydroxide was added. The mixture was stirred at 80° C. for 1 hour. Further, 1.0 g of sodium hydroxide was added, and the mixture was stirred at 80° C. for 1 hour. The mixture was cooled and acidified with concentrated hydrochooric acid, and then extracted with chloroform. The organic layer was washed with water and dried. Then, the solvent was distilled off to obtain a crude product of the above identified compound. The crude product was purified by column chromatography to obtain 1.85 g (yield: 45%) of Compound No. 2 of the present invention.

White crystal, m.p.: 215°-217° C.

NMR (δvalue (CDCl₃)): 0.96 (d, 3H), 1.14 (d, 3H), 1.52 (s, 3H), 1.98-2.45 (m, 1H), 2.99-3.20 (m, 2H), 4.02-4.21 (m, 2H), 4.88 (s, 2H), 8.62 (s, 1H), 9.50-10.50 (b, 2H).

SYNTHETIC EXAMPLE 44

Preparation of

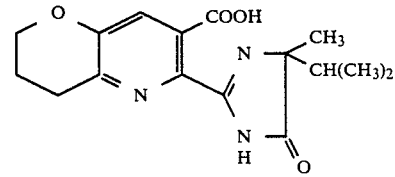

(Compound No. 1 of the present invention)

10.8 g (0.032 mol) of the amide of the formula II-a (wherein

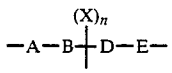

is —O—CH$_2$—CH$_2$—CH$_2$— and Z is CONH$_2$) obtained quantitatively in the same manner as in Synthetic Example 22, was added to 60 ml of an aqueous solution containing 5.6 g of sodium hydroxide. The mixture was stirred under heating at 80° C. for 3 hours.

The mixture was cooled, then adjusted to pH 3 with concentrated hydrochloric acid and extracted with chloroform. The extract was dried, and the solvent was distilled off under reduced pressure. The residue was purified by column chromatography to obtain 3.9 g (yield: 38%) of Compound No. 1 of the present invention.

White crystal, m.p.: 201°–204° C.

SYNTHETIC EXAMPLE 45

Preparation of

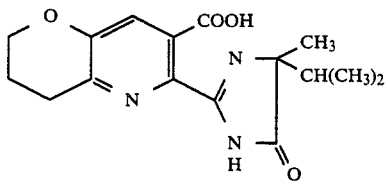

(Compound No. 1 of the present invention)

To a solution comprising 0.5 g of a 37% hydrochloric acid aqueous solution and 0.3 g of water, a solution comprising 0.56 g of the compound of the formula II-a (wherein

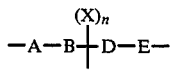

is —O—CH$_2$—CH$_2$—CH$_2$—, R is a hydrogen atom, R$^1$ is a methyl group, R$^2$ is an isopropyl group and Z is CN), 5 ml of toluene and 1.6 g of dimethylsulfoxide, was added. The mixture was stirred at a temperature of 45° C. for one day and night. Then, 11.5 g of a 25% sodium hydroxide aqueous solution was added, and the mixture was stirred at a temperature of 70° C. for 3 hours. The reaction solution was cooled to room temperature, then acidified with concentrated hydrochloric acid and extracted with chloroform. The organic layer was washed with water and then dried. Then, solvent was distilled off under reduced pressure, and the residue was purified by column chromatography to obtain 0.33 g (yield: 59%) of Compound No. 1 of the present invention.

White crystal, m.p.: 201°–204° C.

The compound of the formula I as identified in Table 1 can be prepared by either one of Reaction Schemes 1, 2, 3 and 4. However, the compounds of the present invention are not restricted to these specific Examples.

The compound Nos. identified in Table 1 will be referred to in the following Formulation Examples and Test Examples.

For application as herbicides, the compounds of the present invention may be combined with a suitable carrier, for instance, a solid carrier such as clay, talc, bentonite or diatomaceous earth, or a liquid carrier such as water, an alcohol (such as methanol or ethanol), an aromatic hydrocarbon (such as benzene, toluene or xylene), a chlorinated hydrocarbon, an ether, a ketone, an ester (such as ethyl acetate) or an acid amide (such as dimethylformamide). If necessary, an emulsifier, a dispersant, a suspending agent, a wetting agent, an extender, a stabilizer, etc. may be added to form optional formulations such as a solution, an emulsion, a wettable powder, a dust, a granule, a flowable agent, etc. There is no particular restriction as to the content of the compounds as active ingredients in these formulations. However, the content of the active ingredients is usually within a range of from 1.0 to 90.0% by weight. Further, if necessary, other types of herbicides, various insecticides, fungicides, plant growth controlling agents, assisting agents, etc. may be combined at the time of the formulation or at the time of the application of the herbicides. More specifically, the compounds of the present invention may be used in combination with the following substances:

Naptalam (N-naphthylphthalamic acid), 1,4-DB ($\gamma$-(2,4-dichlorophenoxy)butyric acid), MCPB ($\gamma$-(2-methyl-4-chlorophenoxy)butyric acid), Acifluorfen-Sodium (sodium 5-[2-chloro-4-(trifluoromethyl)phenoxy]-2-nitrobenzoate), Lactofen (1'-(carboethoxy)ethyl-5-[2-chloro-4-(trifluromethyl)phenoxy]-2-nitrobenzoate), fomesafen (5-[2-chloro-4-(trifluoromethyl)phenoxy]-2-nitro-N-methylsulfonylbenzamide), alachlor (2-chloro-2',6'-diethyl-N-(methoxymethyl)acetanilide), metolachlor (2-chloro-2'-ethyl-6'-methyl-N-(2-methoxy-1-methylethyl)acetanilide), bentazone (3-isopropyl-(1H)-2,1,3-benzothiadiazin-4(3H)-one 2,2-dioxide), metribuzin (4-amino-6-tert-butyl-3-methylthio-1,2,4-triazin-5-(4H)-one), ethyl-2-[3-(4-chloro-6-methoxypyridmidin-2-yl) ureidosulfonyl]benzoate, imazaquim (2-(4-isopropyl-4-methyl-5-oxo-2-imidazolin-2-yl)-3-quinolinic acid), 5-ethyl-2-(4-isopropyl-4-methyl-5-oxo-2-imidazolin-2-yl)nicotinic acid, quizalofop-ethyl (ethyl-2-[4-(6-chloro-2-quinoxanyloxy)phenoxy]propionate), dichlofop methyl (methyl-2-[4-(2,4-dichlorophenoxy)-phenoxy]propionate), fluazifop-butyl (butyl-2-[4-(5-trifluoromethyl-2-pyridyloxy)phenoxy]propionate), Sethoxydim (2-(1-ethoxyiminobutyl)-5-[2-(ethylthio)-propyl]-3-hydroxycyclohex-2-enone), Fenoxaprop-ethyl (ethyl-2-[4-(6-chloro-2-benzoxazolyloxy)phenoxy]propionate), haloxyfop-methyl (methyl-2-[4-(3-chloro-5-trifluoromethyl-2-pyridyloxy)phenoxy]propionate) and toxaphene (a reaction mixture of chlorinated camphenes containing 67–69% chlorine).

The above-mentioned other kinds of compounds to be combined with the compounds of the present invention are, for instance, those disclosed in Farm Chemicals Handbook, 72nd edition (1986).

The compounds of the present invention can be applied for the control of various weeds not only in the agricultural and horticultural fields such as uplands, paddy fields, or orchards, but also in non-agricultural fields such as play grounds, open areas or rail road sides. The dose in their application may vary depending upon the application site, the application season, the application manner, the type of weeds to be controlled and the crop plants. However, the dose is usually within a range of from 0.005 to 10 kg per hectare as the amount of active ingredient.

Now, Formulation Examples of the herbicides containing the compounds of the present invention as the active ingredients, will be described. However, the formulations are not restricted to these specific Examples. In the following Formulation Examples, "parts" means "parts by weight".

SOLUTION

Active ingredient: 5-75 parts, preferably 10-50 parts, more preferably 15-40 parts
Liquid carrier: 25-95 parts, preferably 30-88 parts, more preferably 82-40 parts
Surfactant: 1-30 parts, preferably 2-20 parts

EMULSIFIABLE CONCENTRATE

Active ingredient: 2.5-50 parts, preferably 5-45 parts, more preferably 10-40 parts
Surfactant: 1-30 parts, preferably 2-25 parts, more preferably 3-20 parts
Liquid carrier: 20-95 parts, preferably 30-93 parts, more preferably 57-85 parts

DUST

Active ingredient: 0.5-10 parts
Solid carrier: 90-99.5 parts

FLOWABLE AGENT

Active ingredient: 5-75 parts, preferably 10-50 parts
Water: 25-94 parts, preferably 30-90 parts
Surfactant: 1-30 parts, preferably 2-20 parts

WETTABLE POWDER

Active ingredient: 2.5-90 parts, preferably 10-80 parts, more preferably 20-75 parts
Surfactant: 0.5-20 parts, preferably 1-15 parts, more preferably 2-10 parts
Solid carrier: 5-90 parts, preferably 7.5-88 parts, more preferably 16-56 parts

GRANULE

Active ingredient: 0.5-30 parts
Solid carrier: 70-99.5 parts

The solution and emulsifiable concentrate are prepared by dissolving the active ingredients in the respective liquid carriers containing surfactans. The wettable powder is prepared by mixing the surfactant, the solid carrier and the active ingredient and pulverizing the mixture. The dust is prepared by mixing the surfactant, the solid carrier and the active ingredient, and if necessary, pulverizing the mixture. The flowable agent is prepared by suspending or dispersing the active ingredient in an aqueous solution containing the surfactant. The granule is prepared by mixing the active ingredient and the adjuvant.

| Formulation Example 1 Wettable powder | |
|---|---|
| Compound No. 1 of the present invention | 50 parts |
| Zeeklite PFP (tradename for kaolin-type clay, manufactured by Zeeklite Kogyo K.K.) | 43 parts |
| Sorpol 5039 (tradename for a mixture of a nonionic surfactant and an anionic surfactant, manufactured by Toho Kagaku Kogyo K.K.) | 5 parts |
| Carplex (coagulation preventing agent) (tradename for a mixture of a surfactant and white carbon, manufactured by Shionogi & Co. Ltd.) | 2 parts |

The above components are uniformly mixed and pulverized to obtain a wettable powder. In use, the wettable powder is diluted from 10 to 10,000 times and applied so that the dose of the active ingredient will be from 0.005 to 10 kg per hectare.

| Formulation Example 2 Emulsifiable concentrate | |
|---|---|
| Compound No. 1 of the present invention | 10 parts |
| Xylene | 70 parts |
| Dimethylformamide | 10 parts |
| Sorpol 2680 (tradename for a mixture of a nonionic surfactant and an anionic surfactant, manufactured by Toho Kagaku Kogyo K.K.) | 10 parts |

The above components are uniformly mixed to obtain an emulsifiable concentrate. In use, the above emulsifiable concentrate is diluted from 10 to 10,000 times and applied so that the dose of the active ingredient will be from 0.005 to 10 kg per hectare.

| Formulation Example 3 Granule | |
|---|---|
| Compound No. 2 of the present invention | 5 parts |
| Bentonite | 54 parts |
| Talc | 40 parts |
| Calcium lignin sulfonate | 1 part |

The above components are uniformly mixed and pulverized, and a small amount of water was added thereto. The mixture was stirred and mixed. The mixture was granulated by an extrusion-type granulating machine, and dried to obtain granules. In use, the above granules are applied so that the dose of the active ingredient will be from 0.005 to 10 kg per hectare.

| Formulation Example 4 Flowable agent | |
|---|---|
| Compound No. 3 of the present invention | 25 parts |
| Sorpol 3353 (tradename for a nonionic surfactant, manufactured by Toho Kagaku Kogyo K.K.) | 10 parts |
| Runox 1000C (tradename for an anionic surfactant, manufactured by Toho Kagaku Kogyo K.K.) | 0.5 part |
| 1% Xanthan Gum aqueous solution (natural polymer) | 20 parts |
| Water | 44.5 parts |

Sorpol 3353, Runox 1000C and 1% Xanthan Gum aqueous solution were uniformly dissolved in water, and then Compound No. 3 of the present ianvention was added thereto. The mixture was thoroughly mixed, and wet-pulverized by a sand mill to obtain a flowable agent. In use, the above-mentioned flowable agent was diluted from 10 to 10,000 times, and applied so that the dose of the active ingredient will be frofm 0.005 to 10 kg per hectare.

| Formulation Example 5 Wettable powder | |
|---|---|
| Compound No. 2 of the present invention | 50 parts |
| Zeeklite A (tradename for kaolin-type clay, manufactured by Zeeklite Kogyo K.K.) | 46 parts |
| Sorpol 5039 (tradename for a mixture of a nonionic surfactant and an anionic surfactant, manufactured by Toho Kagaku K.K.) | 2 parts |
| Carplex (coagulation preventing agent) (tradename for white carbon, manufactured by Shionogi & Co., Ltd.) | 2 parts |

The above components are uniformly mixed and pulverized to obtain a wettable powder.

| Formulation Example 6 Wettable powder | |
|---|---|
| Compound No. 3 of the present invention | 45 parts |

-continued

| Formulation Example 6 Wettable powder | |
|---|---|
| Zeeklite A (tradename for kaolin-type clay, manufactured by Zeeklite Kogyo K.K.) | 51 parts |
| Sorpol 5039 (tradename for a mixture of a nonionic surfactant and an anionic surfactant, manufactured by Toho Kagaku K.K.) | 2 parts |
| Carplex (coagulation preventing agent) (tradename for white carbon, manufactured by Shionogi & Co., Ltd.) | 4 parts |

The above components are uniformly mixed and pulverized to obtain a wettable powder. In use, the above-mentioned wettable powder is diluted from 10 to 10,000 times, and applied so that the dose of the active ingredient will be from 0.005 to 10 kg per hectare.

| Formulation Example 7 Emulsifiable concentrate | |
|---|---|
| Compound No. 2 of the present invention | 2 parts |
| Xylene | 78 parts |
| Dimethylformamide | 15 parts |
| Sorpol 2680 (tradename for a mixture of a nonionic surfactant and an anionic surfactant, manufactured by Toho Kagaku Kogyo K.K.) | 5 parts |

The above components are uniformly mixed to obtain an emulsifiable concentrate. In use, the above emulsifiable concentrate is diluted from 10 to 10,000 times, and applied so that the dose of the active ingredient will be from 0.005 to 10 kg per hectare.

| Formulaion Example 8 Flowable agent | |
|---|---|
| Compound No. 2 of the present invention | 25 parts |
| Agrisol S-710 (tradename for a nonionic surfactant, manufactured by Kao Corp.) | 10 parts |
| Runox 1000C (tradename for an anionic surfactant, manufactured by Toho Kagaku Kogyo K.K.) | 0.5 part |
| 1% Rodopol water (tradename for a thickener, manufactured by Rhone-Poulenc) | 20 parts |
| Water | 44.5 parts |

The above components are uniformly mixed to obtain a flowable agent.

| Formulation Example 9 Granule | |
|---|---|
| Compound No. 1 of the present invention | 0.1 parts |
| Bentonite | 55.0 parts |
| Talc | 44.9 parts |

The above components are uniformly mixed and pulverized, and a small amount of water was added thereto. The mixture was stirred, mixed and kneaded, and then it was granulated by an extrusion type granulating machine and dried to obtain granules.

| Formulation Example 10 Granule | |
|---|---|
| Compound No. 3 of the present invention | 0.5 part |
| Bentonite | 55.0 parts |
| Talc | 44.5 parts |

The above components are uniformly mixed and pulverized, and a small amount of water was added thereto. The mixture was stirred, mixed and kneaded, and then it was granulated by an extrusion type granulating machine and dried to obtain granules.

| Formulation Example 11 Wettable powder | |
|---|---|
| Compound No. 1 of the present invention | 10 parts |
| Zeeklite PFP (tradename for kaolin-type clay, manufactured by Zeeklite Kogyo K.K.) | 83 parts |
| Sorpol 5039 (tradename for a mixture of a nonionic surfactant and an anionic surfactant, manufactured by Toho Kagaku K.K.) | 5 parts |
| Carplex (coagulation preventing agent) (tradename for white carbon, manufactured by Shionogi & Co., Ltd.) | 2 parts |

The above components are uniformly mixed and pulverized to obtain a wettable powder.

| Formulation Example 12 Wettable powder | |
|---|---|
| Compound No. 29 of the present invention | 20 parts |
| Zeeklite PFP (tradename for kaolin-type clay, manufactured by Zeeklite Kogyo K.K.) | 73 parts |
| Sorpol 5039 (tradename for a mixture of a nonionic surfactant and an anionic surfactant, manufactured by Toho Kagaku K.K.) | 5 parts |
| Carplex (coagulation preventing agent) (tradename for white carbon, manufactured by Shionogi & Co., Ltd.) | 2 parts |

The above components are uniformly mixed and pulverized to obtain a wettable powder.

| Formulation Example 13 Wettable powder | |
|---|---|
| Compound No. 15 of the present invention | 30 parts |
| Zeeklite PFP (tradename for kaolin-type clay, manufactured by Zeeklite Kogyo K.K.) | 63 parts |
| Sorpol 5039 (tradename for a mixture of a nonionic surfactant and an anionic surfactant, manufactured by Toho Kagaku K.K.) | 5 parts |
| Carplex (coagulation preventing agent) (tradename for white carbon, manufactured by Shionogi & Co., Ltd.) | 2 parts |

The above components are uniformly mixed and pulverized to obtain a wettable powder.

| Formulation Example 14 Wettable powder | |
|---|---|
| Compound No. 7 of the present invention | 50 parts |
| Zeeklite PFP (tradename for kaolin-type clay, manufactured by Zeeklite Kogyo K.K.) | 43 parts |
| Sorpol 5039 (tradename for a mixture of nonionic surfactants and anionic surfactants, manufactured by Toho Kagaku K.K.) | 5 parts |
| Carplex (coagulation preventing agent) (tradename for white carbon, manufactured by Shionogi & Co., Ltd.) | 2 parts |

The above components are uniformly mixed and pulverized to obtain a wettable powder.

| Formulation Example 15 Wettable powder | |
|---|---|
| Compound No. 50 of the present invention | 40 parts |
| Zeeklite PFP (tradename for kaolin-type clay, manufactured by Zeeklite Kogyo K.K.) | 53 parts |
| Sorpol 5039 (tradename for a mixture of a nonionic surfactant and an anionic surfactant, manufactured by Toho Kagaku K.K.) | 5 parts |
| Carplex (coagulation preventing agent) (tradename for white carbon, manufactured by Shionogi & Co., Ltd.) | 2 parts |

The above components are uniformly mixed and pulverized to obtain a wettable powder.

| Formulation Example 16 Flowable agent | |
| --- | --- |
| Compound No. 1 of the present invention | 60 parts |
| Agrisol B-710 (tradename for a nonionic surfactant, manufactured Kao Corp.) | 10 parts |
| Runox 1000C (tradename for an anionic surfactant, manufactured by Toho Kagaku Kogyo K.K.) | 0.5 part |
| 1% Rodopol water (tradename for a thickener, manufactured by Rhone-Poulenc | 10 parts |
| Water | 19.5 parts |

The above components are uniformly mixed to obtain a flowable agent. In use, the above-mentioned flowable agent is diluted from 10 to 10,000 times, and applied so that the dose of the active ingredient will be from 0.005 to 10 kg per hectare.

| Formulation Example 17 Wettable powder | |
| --- | --- |
| Compound No. 85 of the present invention | 70 parts |
| Zeeklite PFP (tradename for kaolin-type clay, manufactured by Zeeklite Kogyo K.K.) | 23 parts |
| Sorpol 5039 (tradename for a mixture of a nonionic surfactant and an anionic surfactant, manufactured by Toho Kagaku K.K.) | 5 parts |
| Carplex (coagulation preventing agent) (tradename for white carbon, manufactured by Shionogi & Co., Ltd.) | 2 parts |

The above components are uniformly mixed and pulverized to obtain a wettable powder.

| Formulation Example 18 Emulsifiable concentrate | |
| --- | --- |
| Compound No. 1 of the present invention | 1 part |
| Xylene | 79 parts |
| Dimethylformamide | 15 parts |
| Sorpol 2680 (tradename for a mixture of nonionic surfactant and an anionic surfactant, manufactured by Toho Kagaku Kogyo K.K.) | 5 parts |

The above components are uniformly mixed to obtain an emulsifiable concentrate. In use, the above emulsifiable concentrate is diluted from 10 to 10,000 times, and applied so that the dose of the active ingredient will be from 0.005 to 10 kg per hectare.

| Formulation Example 19 Flowable agent | |
| --- | --- |
| Compound No. 2 of the present invention | 40 parts |
| Agrisol B-710 (tradename for a nonionic surfactant, manufactured Kao Corp.) | 10 parts |
| Runox 1000C (tradename for an anionic surfactant, manufactured by Toho Kagaku Kogyo K.K.) | 0.5 part |
| 1% Rodopol water (tradename for a thickener, manufactured by Rhone-Poulenc) | 20 parts |
| Water | 29.5 parts |

The above components are uniformly mixed to obtain a flowable agent.

| Formulation Example 20 Wettable powder | |
| --- | --- |
| Compound No. 26 of the present invention | 60 parts |
| Zeeklite PFP (tradename for kaolin-type clay, manufactured by Zeeklite Kogyo K.K.) | 33 parts |
| Sorpol 5039 (tradename for a mixture of a nonionic surfactant and an anionic surfactant, manufactured by Toho Kagaku K.K.) | 5 parts |
| Carplex (coagulation preventing agent) (tradename for white carbon, manufactured by Shionogi & Co., Ltd.) | 2 parts |

The above components are uniformly mixed and pulverized to obtain a wettable powder.

| Formulation Example 21 Emulsifiable concentrate | |
| --- | --- |
| Compound No. 3 of the present invention | 1.5 parts |
| Xylene | 78.5 parts |
| Dimethylformamide | 15 parts |
| Sorpol 2680 (tradename for a mixture of a nonionic surfactant and an anionic surfactant, manufactured by Toho.Kagaku Kogyo K.K.) | 5 parts |

The above components are uniformly mixed to obtain an emulsifiable concentrate.

| Formulation Example 22 Granule | |
| --- | --- |
| Compound No. 1 of the present invention | 1.0 parts |
| Bentonite | 55.0 parts |
| Talc | 44.0 parts |

The above components are uniformly mixed and pulverized, and a small amount of water was added thereto. The mixture was stirred, mixed and kneaded, and then it was granulated by an extrusion type granulating machine and dried to obtain granules.

| Formulation Example 23 Emulsifiable concentrate | |
| --- | --- |
| Compound No. 3 of the present invention | 2 parts |
| Xylene | 78 parts |
| Dimethylformamide | 15 parts |
| Sorpol 2680 (tradename for a mixture of a nonionic surfactant and an anionic surfactants, manufactured by Toho Kagaku Kogyo K.K.) | 5 parts |

The above components are uniformly mixed to obtain an emulsifiable concentrate. In use, the above emulsifiable concentrate is diluted from 10 to 10,000 times, and applied so that the dose of the active ingredient will be from 0.005 to 10 kg per hectare.

| Formulation Example 24 Flowable agent | |
| --- | --- |
| Compound No. 1 of the present invention | 10 parts |
| Agrisol B-710 (tradename for a nonionic surfactant, manufactured by Kao Corp.) | 10 parts |
| Runox 1000C (tradename for an anionic surfactant, manufactured by Toho Kagaku Kogyo K.K.) | 0.5 part |
| 1% Rodopol water (tradename for a thickener, manufactured by Rhone-Poulenc) | 20 parts |
| Water | 59.5 parts |

The above components are uniformly mixed to obtain a flowable agent.

| Formulation Example 25 Solution | |
| --- | --- |
| Compound No. 84 of the present invention | 20 parts |
| Sorpol W-150 (tradename for a nonionic surfactant, manufactured by Toho Kagaku Kogyo K.K.) | 10 parts |
| Water | 70 parts |

The above components are uniformly mixed to obtain solution. In use, the above solution is diluted from 10 to 10,000 times, and applied so that the dose of the active ingredient will be from 0.005 to 10 kg per hectare.

| Formulation Example 26 Solution | |
|---|---|
| Compound No. 28 of the present invention | 30 parts |
| Nippol W-150 (tradename for a nonionic surfactant, manufactured by Nissan Chemical Industries Ltd.) | 10 parts |
| Water | 60 parts |

The above components are uniformly mixed to obtain solution. In use, the above solution is diluted from 10 to 10,000 times, and applied so that the dose of the active ingredient will be from 0.005 to 10 kg per hectare.

| Formulation Example 27 Solution | |
|---|---|
| Compound No. 28 of the present invention | 10 parts |
| Sorpol W-150 (tradename for a nonionic surfactant, manufactured by Toho Kagaku Kogyo K.K.) | 10 parts |
| Water | 80 parts |

The above components are uniformly mixed to obtain solution. In use, the above solution is diluted from 10 to 10,000 times, and applied so that the dose of the active ingredient will be from 0.005 to 10 kg per hectare.

Now, the usefulness of the compounds of the present invention as herbicides will be specifically described with reference to the following Test Examples.

TEST EXAMPLE 1

Test on the Herbicidal Effects in Soil Treatment

A plastic box having a length of 30 cm, a width of 22 cm, and a depth of 6 cm was filled with a sterilized deluvium soil and seeds of rice (*Oryza sativa*), barnyardgrass (*Echinochloa crus-galli*), annular sedge (*Cyperus microiria*), black nightshade (*Solanum nigrum* L.), rorippa ssp. (*Rorippa atrovirens*), corn (*Zea mays*), wheat (*Triticum vulgare*), soybean (*Glysine max*), cotton (*Gossypium*) and galinsoga spp. (*Galinsoga ciliata*) were sown. the soil was covered thereon in the thickness of about 1.5 cm, and then a solution was applied onto the surface of the soil to distribute the active ingredient uniformly at a predetermined concentration.

Each solution was prepared by diluting the solution, wettable powder, emulsifiable concentrate or flowable agent described in the above Formulation Examples with water and sprayed onto the entire soil surface by means of a small spray. three weeks after the application of the solution, the herbicidal effects against each weed were determined on the basis of following standard rating.

STANDARD RATING

5: Growth control rate of more than 90% (almost completely withered)
4: Growth control rate of from 70 to 90%
3: Growth control rate of from 40 to 70%
2: Growth control rate of from 20 to 40%
1: Growth control rate of from 5 to 20%
0: Growth control rate of less than 5% (almost non-effective)

The above growth control rates were calculated by the following equation:

$$\text{Growth control rate (\%)} = \left[ 1 - \frac{\text{Weight of the weed grown above the soil surface of the treated area}}{\text{Weight of the weed grown above the soil surface of the non-treated area}} \right] \times 100$$

Further, the phytotoxicity against each crop plant was determined on the basis of the following standard rating. The results are shown in Table 2.

STANDARD RATING

5: Complete death of the crop plant
4: Serious phytotoxicity to the crop plant
3: Fair phytotoxicity to the crop plant
2: Slight phytotoxicity to the crop plant
1: Extremely slight phytotoxicity to the crop plant
0: No phytotoxicity to the crop plant

TEST EXAMPLE 2

Test on Herbicidal Effects and Phytotoxicity in Foliage Treatment

A plastic box having a length of 30 cm, a width of 22 cm and a depth of 6 cm was filled with a sterilized deluvium soil, and seeds of rice (*Oryza sativa*), barnyardgrass (*Echinochloa crus-galli*), annual sedge (*Cyperus microiria*), black nightshade (*Solanum nigrum* L.), rorippa ssp. (*Rorippa atrovirens*), corn (*Zea mays*), wheat (*Triticum vulgare*), soybean (*Glysine max*), cotton (*Gossypium*), galinsoga spp. (*Galinsoga ciliata*) and sugar beet (*Beta vulgaris*) were spot-wisely sown. The soil was covered thereon in a thickness of about 1.5 cm. When the various plants grew to the 2-3 leaf stage, a solution was uniformly sprayed onto the foliages to distribute the active ingredient at a predetermined dose. Each solution was prepared by diluting the solution, wettable powder, emulsifiable concentrate or flowable powder described in above Formulation Examples with water and sprayed to the entire surface of the foliages of the weeds and the crop plants by a small spray. Four weeks after the application of the solution, the herbicidal effects against each weed and the phytotoxicity against each crop plant were determined on the basis of the standard rating described in Test Example 1. The results thereby obtained are shown in Table 3.

TEST EXAMPLE 3

Test on the Application for the Cultivation of Soybeans (Foliage Treatment)

A plastic box having a diameter of 30 cm and a depth of 12 cm was filled with a sterilized deluvium soil, and seeds of soybean (*Glysine max*), Johnsongrass (*Sorghum halepense*), barnyardgrass (*Echinochloa crus-galli*), green foxtail (*Setaria viridis*), goosegrass (*Eleusine indica*), cocklebur (*Xanthium strumarium*), Jimsonweed (*Datura stramonium*), tall morningglory (*Ipomoea purpurea*), velvet leaf (*Abutilon theophrasti*), prickly sida (*Sida spinosa*), livid amaranth (*Amaranthus lividus*) and hemp sesbania (*Sesbania exaltata*) were sown, and the soil was covered thereon in a thickness of about 1.5 cm. Further, purple nutsedge (*Cyperus rotundus*) tubers are planted in a separate pot in a depth of 1.5 cm. When the various plants grew to the 1 leaf stage, a solution was uniformly sprayed onto the foliages to distribute the active ingredient at a predetermined dose. Each solution was prepared by diluting the wettable powder described in above Formulation Examples with water and sprayed to the entire surface of the foliages of the plants by a small spray. Four weeks after the application of the solution, the herbicidal effects against each plant were determined on the basis of the standard rating described in Test Example 1. The results thereby obtained are shown in Table 4.

TABLE 1

$$(X)_n \begin{array}{c} \text{structure with pyridine ring, substituents A-B and D-E, COOR, and side chain} \\ \text{N-CH(CH}_3\text{)(CH(CH}_3\text{)}_2\text{)-NH-C(=W)} \end{array}$$

| Compound No. | $(X)_n$ −A−B−+−D−E− | R | W | Characteristics | Melting point (°C.) |
|---|---|---|---|---|---|
| 1 | −O−CH$_2$−CH$_2$−CH$_2$− | H | O | White crystal | 201–204 |
| 2 | −CH$_2$−O−CH$_2$−CH$_2$− | H | O | White crystal | 215–217 |
| 3 | −CH=CH−CH$_2$−CH$_2$− | H | O | White crystal | 201.6–206.3 |
| 4 | −CH=CH−CH$_2$−CH$_2$− | H | S | | |
| 5 | −S−CH$_2$−CH$_2$−CH$_2$− | Na$^+$ | O | White crystal | 247–260 (decomposed) |
| 6 | −O−CH$_2$−CH$_2$−CH$_2$− | −C(Me)(Me)−CH=CH$_2$ | O | | |
| 7 | −C(=O)−CH$_2$−C(Me)$_2$−CH$_2$− | H | O | White crystal | 213–216 |
| 8 | −S−CH$_2$−CH$_2$−CH$_2$− | CH$_2$SCH$_3$ | O | | |
| 9 | −CH$_2$−S−CH$_2$−CH$_2$− | H | S | | |
| 10 | −C(=O)−CH$_2$−CH$_2$−CH$_2$− | iPrNH$_3^+$ | O | | |
| 11 | −CH$_2$−O−CH=CH− | H | O | | |
| 12 | −CH$_2$−O−CH$_2$−CH$_2$− | iPrNH$_3^+$ | O | Glassy substance | |
| 13 | −CH=CH−CH$_2$−CH$_2$− | iPrNH$_3^+$ | O | White crystal | 140–205 |
| 14 | −S−CH$_2$−CH$_2$−CH$_2$− | H | S | | |
| 15 | −S−CH$_2$−CH$_2$−CH$_2$− | H | O | White crystal | 216–217 |
| 16 | −CH=CH−C(Me)$_2$−CH$_2$− | H | S | | |
| 17 | −CH$_2$−SO$_2$−CH$_2$−CH$_2$− | H | O | Glassy substance | |
| 18 | −CH$_2$−CH$_2$−N(Me)−CH$_2$− | H | O | | |
| 19 | −CH=CH−CH$_2$−CH$_2$− | −C(Me)(Me)−CH=CH$_2$ | O | | |
| 20 | −CH=CH−C(Me)$_2$−CH$_2$− | Et | O | | |
| 21 | −CH$_2$−S−CH$_2$−CH$_2$− | −CH$_2$C≡CH | O | | |
| 22 | −CH=CH−C(Me)$_2$−CH$_2$− | Me | O | | |

TABLE 1-continued

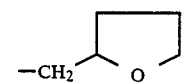

| Compound No. | —A—B—(X)n—D—E— | R | W | Characteristics | Melting point (°C.) |
|---|---|---|---|---|---|
| 23 | —CH₂—CH₂—O—CH₂— | CH₂SCH₃ | O | | |
| 24 | —CH₂—CH₂—S—CH₂— | H | O | | |
| 25 | —O—CH₂—CH=CH— | H | O | | |
| 26 | —C(=O)—CH₂—CH₂—CH₂— | H | O | White crystal | 260–263 |
| 27 | —CH₂—CH₂—CH₂—S— | H | O | | |
| 28 | —O—CH₂—CH₂—CH₂— | iPrNH₃⁺ | O | White crystal | 132–145 (decomposed) |
| 29 | —CH=CH—C(Me)(Me)—CH₂— | H | O | White crystal | 209–212 |
| 30 | —CH=CH—CH(2,4,6-trimethylphenyl)—CH₂— | H | O | | |
| 31 | —CH₂—O—CH₂—CH(Cl)— | H | O | | |
| 32 | —O—CH₂—CH₂—CH₂— | —CH₂C≡CH | O | | |
| 33 | —CH₂—O—CH₂—CH₂— | —CH₂C≡CH | O | White crystal | 194–199 |
| 34 | —CH=CH—CH(3-tetrahydrothiopyranyl)—CH₂— | H | O | | |
| 35 | —O—CH—CH₂—CH₂— | —CH₂SCH₃ | O | | |
| 36 | —CH₂—O—CH₂—CH₂— | —CH₂SCH₃ | O | | |
| 37 | —O—CH=CH—CH₂— | H | O | | |
| 38 | —C(=O)—CH₂—CH₂—CH₂— | Na⁺ | O | | |
| 39 | —C(=O)—CH₂—CH(3-tetrahydrothiopyranyl)—CH₂— | H | O | | |
| 40 | —CH₂—CH₂—CH₂—O— | H | S | | |
| 41 | —O—CH₂—CH₂—CH₂— | —CH₂-(tetrahydrofuran-2-yl) | O | | |
| 42 | —O—CH₂—CH₂—CH₂— | H | S | | |
| 43 | —CH=CH—C(Me)(Me)—CH₂— | CH₂SCH₃ | O | | |
| 44 | —CH=CH—C(Me)(Me)—CH₂— | —C(Me)(Me)—CH=CH₂ | O | | |
| 45 | —CH₂—O—CH₂—CH(OMe)— | H | O | | |

TABLE 1-continued

Structure: pyridine ring with substituents A-B-(X)n-D-E forming a fused ring, COOR group, and imidazolinone side chain with CH₃, CH(CH₃)₂ groups, NH, and =W.

| Compound No. | —A—B—⟨(X)n⟩—D—E— | R | W | Characteristics | Melting point (°C.) |
|---|---|---|---|---|---|
| 46 | —CH(Me)—O—CH(Me)—CH₂— | H | O | White crystal | 218–221 |
| 47 | —CH₂—O—CH₂—CH₂— | Et | O | | |
| 48 | —CH₂—CH₂—O—CH₂— | Na⁺ | O | | |
| 49 | —CH=CH—O—CH₂— | H | O | | |
| 50 | —CH₂—S—CH₂—CH₂— | H | O | White crystal | 190–192 |
| 51 | —CH₂—CH₂—O—CH₂— | iPrNH₃⁺ | O | | |
| 52 | —CH=CH—C(Me)(Me)—CH₂— | iPrNH₃⁺ | O | White crystal | 209–212 |
| 53 | —C(=O)—CH₂—CH₂—CH₂— | Me | O | | |
| 54 | —C(=O)—CH₂—CH(2,4,6-trimethylphenyl)—CH₂— | H | O | | |
| 55 | —CH=CH—C(Me)(Me)—CH₂— | Na⁺ | O | | |
| 56 | —S—CH(OH)—CH₂—CH₂— | H | O | | |
| 57 | —CH₂—CH₂—O—CH₂— | —C(Me)(Me)—CH=CH₂ | O | | |
| 58 | —O—CH₂—CH₂—CH₂— | Me | O | White crystal | 142–143 |
| 59 | —S—CH₂—CH₂—CH₂— | Me | O | | |
| 60 | —CH=CH—CH₂—CH₂— | Et | O | | |
| 61 | —CH₂—CH₂—S—CH₂— | CH₂SCH₃ | O | | |
| 62 | —C(=O)—CH₂—CH₂—CH₂— | CH₂SCH₃ | O | | |
| 63 | —CH₂—CH₂—O—CH(Me)— | H | O | | |
| 64 | —CH₂—O—CH(Me)—CH₂— | H | O | | |
| 65 | —CH₂—O—CH₂—CH₂— | —C(Me)(Me)—CH=CH₂ | O | | |
| 66 | —CH₂—N(Et)—CH₂—CH₂— | H | O | | |

TABLE 1-continued

| Compound No. | —A—B—[(X)n]—D—E— | R | W | Characteristics | Melting point (°C.) |
|---|---|---|---|---|---|
| 67 | —C(=O)—CH₂—CH₂—CH₂— | —C(Me)(Me)—CH=CH₂ | O | | |
| 68 | —CH=CH—C(Me)(Me)—CH₂— | —CH₂C≡CH | | | |
| 69 | —CH=CH—CH₂—CH₂— | Me | O | White crystal | 158–164 |
| 70 | —CH₂—CH₂—CH₂—O— | H | O | | |
| 71 | —CH₂—CH₂—O—CH₂— | tetrahydrofuryl (O in ring) | O | | |
| 72 | —CH=CH—CH₂—CH₂— | CH₂SCH₃ | O | White crystal | 198–202 |
| 73 | —CH₂—O—CH₂—CH₂— | Me | O | White crystal | 229–233 |
| 74 | —S—CH₂—CH₂—CH₂— | —CH₂C≡CH | O | White crystal | 154–156 |
| 75 | —CH₂—S(→O)—CH₂—CH₂— | H | O | White crystal | 228–230 |
| 76 | —CH₂—O—CH₂—CH₂— | H | S | | |
| 77 | —C(=O)—CH₂—CH₂—CH₂— | H | S | | |
| 78 | —CH₂—CH₂—O—CH₂— | —CH₂C≡CH | O | | |
| 79 | —C(=O)—CH₂—C(Me)(Me)—CH(CO₂Me)— | H | O | | |
| 80 | —CH=CH—CH₂—CH₂— | Na⁺ | O | White crystal | 260< |
| 81 | —CH₂—N(Me)—CH₂—CH₂— | H | O | | |
| 82 | —CH₂—O—CH₂—CH₂— | Na⁺ | O | | |
| 83 | —CH₂—CH₂—O—CH₂— | Me | O | White crystal | 140–142 |
| 84 | —O—CH₂—CH₂—CH₂ | Na⁺ | O | White crystal | 235–245 (decomposed) |
| 85 | —CH₂—CH₂—O—CH₂— | H | O | White crystal | 155–159 |
| 86 | —CH₂—CH₂—O—CH₂— | H | S | | |
| 87 | —CH=CH—CH₂—CH₂— | —CH₂C≡CH | O | White crystal | 169–175 |
| 88 | —CH₂—S—CH₂—CH₂— | Na⁺ | O | | |
| 89 | —CH(OH)—S—CH₂—CH₂— | H | O | | |

TABLE 1-continued

| Compound No. | —A—B—(X)ₙ—D—E— | R | W | Characteristics | Melting point (°C.) |
|---|---|---|---|---|---|
| 90 | —C(=O)—CH₂—CH(CH₂CHSEt·Me)—CH₂— | H | O | | |
| 91 | —CH=CH—CH(CH₂CHSEt·Me)—CH₂— | H | O | | |
| 92 | —S—CH₂—CH₂—CH₂— | iPrNH₃⁺ | O | White crystal | 209–218 |
| 93 | —S—CH₂—CH₂—CH₂— | —CH₂—C(Me)=CH₂ | O | | |
| 94 | —C(Me)=CH—CH₂—CH₂— | H | O | | |
| 95 | —O—CH₂—CH(CH₂CHSEt·Me)—CH₂— | Na⁺ | O | | |
| 96 | —O—CH₂—CH=CH— | —C(Me)(Me)—CH=CH₂ | O | | |
| 97 | —O—CH₂—CH(Me)—CH₂— | Me | O | | |
| 98 | —O—CH(Me)—CH₂—CH₂— | Na⁺ | O | | |
| 99 | —CH₂—CH₂—O—CH(Me)— | H | O | | |
| 100 | —O—CH=CH—CH₂— | —C(Me)(Me)—C=CH₂ | O | | |
| 101 | —O—CH=CH—CH(Me)— | H | O | | |
| 102 | —CH=C(Me)—O—CH₂— | H | O | | |
| 103 | —CH(Me)—O—CH₂—CH₂— | H | O | | |
| 104 | —O—CH₂—CH=CH— | Na⁺ | O | | |

TABLE 1-continued

Structure: pyridine with substituents -A-B-(X)n-D-E- forming ring, COOR group, and side chain N=C(CH3)(CH(CH3)2)-C(=W)-NH-

| Compound No. | -A-B-(X)n-D-E- | R | W | Characteristics | Melting point (°C.) |
|---|---|---|---|---|---|
| 105 | -S-CH(OMe)-CH₂-CH₂- | H | O | | |
| 106 | -O-CH₂-CH(CF₃)-CH₂- | Me | O | | |
| 107 | -S-CH=CH-CH₂- | H | O | | |
| 108 | -S-CH₂-CH-CH- | H | O | | |
| 109 | -O-CH₂-CH(phenyl)-CH₂- | H | O | | |
| 110 | -O-CH₂-CH(Me)-CH(Me)- | H | O | | |
| 111 | -O-CH₂-CH=C(Me)- | H | O | | |
| 112 | -CH₂-O-CH₂-CH(Me)- | H | O | | |
| 113 | -O-CH(Me)-CH(Me)-CH₂- | H | O | | |
| 114 | -O-CH₂-CH=CH- | -CH₂C≡CH | O | | |
| 115 | -O-CH(Me)-CH₂-CH(Me)- | H | O | | |
| 116 | -O-CH(Me)-CH=C(Me)- | H | O | | |
| 117 | -O-CH₂-CH₂-CH(Cl)- | H | O | | |
| 118 | -O-CH=CH=C(Me)(Me)- | H | O | | |
| 119 | -CH₂-O-C(Me)(Me)-CH₂- | H | O | | |
| 120 | -O-CH₂-CH=CH- | -CH₂SMe | O | | |
| 121 | -O-CH₂-CH₂-CH(Cl)- | Me | O | | |
| 122 | -O-CH₂-CH₂-CH₂- | ⁺NHEt₃ | O | | |
| 123 | -O-CH₂-CH₂-CH₂- | -CH₂-C(Me)=CH₂ | O | | |

TABLE 1-continued

| Compound No. | —A—B—(X)n—D—E— | R | W | Characteristics | Melting point (°C.) |
|---|---|---|---|---|---|
| 124 | —O—C(Me)=CH—CH(Me)— | H | O | | |
| 125 | —O—CH₂—CH(Cl)—CH₂— | H | O | | |
| 126 | —O—C(Me)(Me)—CH₂—CH₂— | H | O | | |
| 127 | —CH=CH—O—CH(Me)— | H | O | | |
| 128 | —CH₂—CH₂—CH=CH— | H | O | | |
| 129 | —O—CH=C(Me)—CH(Me)— | H | O | | |
| 130 | —O—CH(Et)—CH₂—CH₂— | —CH₂C≡CH | O | | |
| 131 | —O—C(Me)=CH—CH₂— | H | O | | |
| 132 | —O—CH(Me)—CH=CH— | H | O | | |
| 133 | —S—CH₂—CH(Me)—CH₂— | H | O | | |
| 134 | —O—CH₂—CH(CH₂—CH(Me)—SEt)—CH₂— | H | O | | |
| 135 | —S—CH₂—CH₂—CH(Me)— | H | O | | |
| 136 | —O—CH₂—CH(3-Cl—5-CF₃-2-pyridyl)—CH₂— | iPrNH₃⁺ | O | | |
| 137 | —CH(Me)—CH₂—CH=CH— | H | O | | |
| 138 | —O—CH₂—C(Me)(Me)—CH₂— | H | O | | |
| 139 | —O—CH=CH—CH₂— | iPrNH₃⁺ | O | | |

TABLE 1-continued

| Compound No. | —A—B—(X)n—D—E— | R | W | Characteristics | Melting point (°C.) |
|---|---|---|---|---|---|
| 140 | —CH$_2$—CH(Me)—O—CH(Me)— | H | O | | |
| 141 | —CH$_2$—CH$_2$—CH=CH— | iPrNH$_3^+$ | O | | |
| 142 | —CH$_2$—CH$_2$—CH=CH— | Na$^+$ | O | | |
| 143 | —O—CH$_2$—C(Me)(Me)—CH$_2$— | —C(Me)(Me)—C=CH$_2$ | O | | |
| 144 | —O—CH(3-Cl—5-CF$_3$—2-pyridyl)—CH$_2$—CH$_2$— | H | O | | |
| 145 | —O—CH(Me)—CH$_2$—CH$_2$— | H | O | | |
| 146 | —O—CH$_2$—CH$_2$—CH$_2$— | K$^+$ | O | | |
| 147 | —O—CH=CH—CH$_2$— | Me | O | | |
| 148 | —S—CH(Me)—CH$_2$—CH$_2$— | H | O | | |
| 149 | —O—CH$_2$—CH$_2$—CH(Et)— | Et | O | | |
| 150 | —CH=C(Me)—CH$_2$—CH$_2$— | H | O | | |
| 151 | —O—CH=CH—CH$_2$— | —CH$_2$C≡CH | O | | |
| 152 | —O—CH(3-Cl—5-CF$_3$—2-pyridyl)—CH$_2$—CH$_2$— | —CH$_2$C≡CH | O | | |
| 153 | —C(Me)=CH—O—CH$_2$— | H | O | | |
| 154 | —O—CH$_2$—CH=CH— | iPrNH$_3^+$ | O | | |
| 155 | —O—CH$_2$—CH$_2$—CH(CF$_3$)— | H | O | | |
| 156 | —O—CH$_2$—CH$_2$—C(Me)(Me)— | Na$^+$ | O | | |
| 157 | —O—CH$_2$—CH$_2$—CH$_2$— | H | O | Optical isomer (S—form) | |
| 158 | —O—CH=CH—CH$_2$— | —CH$_2$SMe | O | | |
| 159 | —O—CH$_2$—CH$_2$—CH$_2$— | H | O | Optical isomer (R—form) | |
| 160 | —O—CH=CH—CH$_2$— | Et | O | | |
| 161 | —S—CH(Cl)—CH$_2$—CH$_2$— | H | O | | |

TABLE 1-continued

| Compound No. | —A—B$\underset{\mid}{(X)_n}$D—E— | R | W | Characteristics | Melting point (°C.) |
|---|---|---|---|---|---|
| 162 | —O—CH$_2$—CH$_2$—CH(OMe)— | —CH$_2$SMe | O | | |
| 163 | —O—CH$_2$—CH$_2$—CH(Me)— | H | O | | |
| 164 | —CH$_2$—O—CH$_2$—CH$_2$— | H | O | Optical isomer (S—form) | |
| 165 | —O—CH$_2$—CH(Me)—CH$_2$— | H | O | | |
| 166 | —CH$_2$—O—CH$_2$—CH$_2$— | H | O | Optical isomer (R—from) | |
| 167 | —O—CH=CH—CH$_2$— | H | S | | |
| 168 | —O—CH$_2$—CH$_2$—CH$_2$— | —CH$_2$—CH(—O—)CH$_2$ (epoxide) | O | | |
| 169 | —CH=CH—CH$_2$—CH$_2$— | H | O | Optical isomer (R—form) | |
| 170 | —O—CH$_2$—CH(OMe)—CH$_2$— | H | O | | |
| 171 | —O—CH(Me)—CH(Me)—CH$_2$— | —C(Me)(Me)—CH=CH$_2$ | O | | |
| 172 | —O—CH(Me)—CH$_2$—CH(Me)— | iPrNH$_3^+$ | O | | |
| 173 | —CH$_2$—CH(Me)—O—CH$_2$— | H | O | | |
| 174 | —O—C(Me)(Me)—CH$_2$—CH$_2$— | H | S | | |
| 175 | —O—CH$_2$—CH$_2$—CH(OH)— | H | O | | |
| 176 | —O—CH$_2$—CH(Et)—CH$_2$ | —CH$_2$SMe | O | | |
| 177 | —O—CH$_2$—CH=CH— | Me | S | | |
| 178 | —O—CH(CF$_3$)—CH$_2$—CH$_2$— | H | O | | |
| 179 | —CH(Me)—CH$_2$—O—CH$_2$— | H | O | | |
| 180 | —CH$_2$—CH$_2$—O—CH$_2$— | H | O | Optical isomer (R—form) | |

TABLE 1-continued

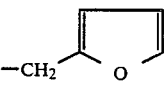

| Compound No. | —A—B—$\overset{(X)_n}{\underset{\phantom{x}}{\text{—}}}$D—E— | R | W | Characteristics | Melting point (°C.) |
|---|---|---|---|---|---|
| 181 | —O—CH$_2$—CH$_2$—CH—<br>　　　　　　　　　｜<br>　　　　　　　　　OMe | H | O | | |
| 182 | —O—CH$_2$—CH$_2$—CH$_2$— | —CH$_2$-(2-furyl) | O | | |
| 183 | 　　　Me<br>　　　｜<br>—O—C—CH=CH—<br>　　　｜<br>　　　Me | H | O | | |
| 184 | —O—CH$_2$—CH$_2$—CH—<br>　　　　　　　　　｜<br>　　　　　　　4-chlorophenyl | H | O | | |
| 185 | —S—CH$_2$—CH$_2$—CH$_2$— | H | O | Optical isomer (R—form) | |
| 186 | —O—CH$_2$—CH$_2$—CH—<br>　　　　　　　　　｜<br>　　　　　　　　　Et | H | O | | |
| 187 | —O—CH—CH$_2$—CH$_2$—<br>　　　｜<br>　　　CF$_3$ | Na$^+$ | O | | |
| 188 | 　　　　　　　　　Me<br>　　　　　　　　　｜<br>—O—CH$_2$—CH$_2$—C—<br>　　　　　　　　　｜<br>　　　　　　　　　Me | H | O | | |
| 189 | —O—CH$_2$—CH$_2$—CH—<br>　　　　　　　　　｜<br>　　　　　　　　　Me | iPrNH$_3^+$ | O | | |
| 190 | 　　　Me<br>　　　｜<br>—CH$_2$—C—O—CH$_2$—<br>　　　｜<br>　　　Me | H | O | | |
| 191 | —O—CH=C—CH$_2$—<br>　　　　　｜<br>　　　　　Me | H | O | | |
| 192 | —O—CH$_2$—CH$_2$—CH—<br>　　　　　　　　　｜<br>　　　　　　　　　CF$_3$ | H | S | | |
| 193 | —O—CH—CH$_2$—CH$_2$—<br>　　　｜<br>　　　Et | H | O | | |
| 194 | —O—CH$_2$—CH—CH$_2$—<br>　　　　　　｜<br>　　　　　　CF$_3$ | H | O | | |
| 195 | —O—CH$_2$—CH=CH— | Et | O | | |
| 196 | —O—CH$_2$—C=CH—<br>　　　　　｜<br>　　　　　Me | H | O | | |

TABLE 1-continued

| Compound No. | —A—B—(X)n—D—E— | R | W | Characteristics | Melting point (°C.) |
|---|---|---|---|---|---|
| 197 | —CH=C(Me)—CH(Me)—CH$_2$— | H | O | | |
| 198 | —O—CH=CH—CH$_2$— | Na$^+$ | O | | |
| 199 | —O—CH$_2$—CH(Br)—CH$_2$— | H | O | | |
| 200 | —O—CH(Phenyl)—CH$_2$—CH$_2$— | H | O | | |
| 201 | —O—CH$_2$—CH$_2$—CH(OCHF$_2$)— | H | O | | |
| 202 | —O—CH$_2$—CH(3-Cl—4-CF$_3$—2-pyridyl)—CH$_2$— | H | O | | |
| 203 | —O—CH(Me)—C(Me)=CH— | H | O | | |
| 204 | —O—CH$_2$—CH(OCF$_3$)—CH$_2$— | H | O | | |
| 205 | —O—CH$_2$—CH(Et)—CH$_2$— | H | O | | |
| 206 | —O—CH$_2$—CH(OCF$_3$)—CH$_2$— | —C(Me)(Me)—CH=CH$_2$ | O | | |
| 207 | —O—CH$_2$—CH(4-methoxyphenyl)—CH$_2$— | H | O | | |
| 208 | —O—CH$_2$—CH(OMe)—CH$_2$— | Et | O | | |
| 209 | —O—CH$_2$—CH(Me)—CH(Me)— | —CH$_2$C≡CH | O | | |
| 210 | —O—CH$_2$—CH$_2$—CH$_2$— | Me$_2$NH$_2^+$ | O | | |
| 211 | —O—CH$_2$—CH$_2$—CH(2-pyridyl)— | H | O | | |
| 212 | —O—CH$_2$—CH=CH— | Me | O | | |
| 213 | —CH$_2$—CH$_2$—C(Me)=CH— | H | O | | |
| 214 | —O—CH$_2$—CH$_2$—CH(OCHF$_2$)— | iPrNH$_3^+$ | O | | |

TABLE 1-continued

[Structure shown: pyridine ring with substituents A, B, D, E, (X)n, COOR, and side chain with N, CH3, CH(CH3)2, NH, =W]

| Compound No. | —A—B—(X)n—D—E— | R | W | Characteristics | Melting point (°C.) |
|---|---|---|---|---|---|
| 215 | —CH₂—CH₂—CH=CH— | —CH₂—C(Me)=CH₂ | O | | |
| 216 | —O—CH₂—CH₂—CH(phenyl)— | H | O | | |
| 217 | —O—CH₂—CH₂—CH(Br)— | H | O | | |
| 218 | —CH₂—CH₂—CH=CH— | Me | O | | |
| 219 | —O—CH₂—CH₂—CH(OH)— | Na⁺ | O | | |
| 220 | —CH₂—CH(Me)—CH=CH— | H | O | | |
| 221 | —O—CH₂—CH₂—CH₂— | Ca²⁺/2 | O | | |
| 222 | —CH₂—S—CH₂—CH₂— | Me | O | | |

Note:
Me: CH₃, Et: C₂H₅, i-Pr: (CH₃)₂CH

TABLE 2

| Compound No. | Dose of active ingredient (kg/ha) | Barn-yard-grass | Annual sedge | Black night-shade | Rorippa ssp. | Rice | Corn | Wheat | Soy-bean | Cotton | Galinsoga spp. |
|---|---|---|---|---|---|---|---|---|---|---|---|
| 1 | 0.16 | 5 | 5 | 5 | 5 | 5 | 5 | 5 | 0 | 5 | 5 |
|   | 0.32 | 5 | 5 | 5 | 5 | 5 | 5 | 5 | 0 | 5 | 5 |
|   | 0.63 | 5 | 5 | 5 | 5 | 5 | 5 | 5 | 0 | 5 | 5 |
| 2 | 0.16 | 3 | 5 | 4 | 4 | 4 | 4 | 4 | 0 | 4 | 3 |
|   | 0.32 | 4 | 5 | 5 | 5 | 5 | 5 | 5 | 0 | 5 | 4 |
|   | 0.63 | 5 | 5 | 5 | 5 | 5 | 5 | 5 | 0 | 5 | 5 |
| 3 | 0.32 | 5 | 5 | 5 | 5 | 5 | 5 | 5 | 0 | 5 | 5 |
|   | 0.63 | 5 | 5 | 5 | 5 | 5 | 5 | 5 | 0 | 5 | 5 |
| 15 | 0.16 | 4 | 4 | 4 | 4 | 2 | 5 | 5 | 0 | 1 | 3 |
|   | 0.32 | 5 | 5 | 5 | 5 | 4 | 5 | 5 | 0 | 2 | 4 |
|   | 0.63 | 5 | 5 | 5 | 5 | 5 | 5 | 5 | 0 | 4 | 5 |
| 26 | 0.63 | 3 | 4 | 5 | 5 | 5 | 5 | 5 | 0 | 2 | 4 |
| 29 | 0.63 | 5 | 4 | 5 | 5 | 5 | 5 | 5 | 0 | 5 | 5 |
| 50 | 0.63 | 4 | 5 | 5 | 5 | 5 | 5 | 5 | 0 | 4 | 5 |
| 85 | 0.16 | 3 | 5 | 5 | 5 | 5 | 5 | 5 | 0 | 4 | 3 |
|   | 0.32 | 5 | 5 | 5 | 5 | 5 | 5 | 5 | 0 | 5 | 5 |
|   | 0.63 | 5 | 5 | 5 | 5 | 5 | 5 | 5 | 0 | 5 | 5 |
| (A)* | 0.63 | 4 | 3 | 5 | 5 | 5 | 4 | 4 | 2 | 1 | 5 |

(A)*: Comparative compound "Linuron" (common name) having the following formula:

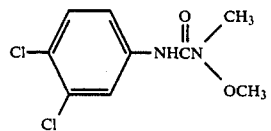

TABLE 3

| Compound No. | Dose of active ingredient (kg/ha) | Barn-yard-grass | Annual sedge | Black night shade | Rorippa ssp. | Galinsoga spp. | Rice | Corn | Wheat | Soy-bean | Cotton | Sugar beet |
|---|---|---|---|---|---|---|---|---|---|---|---|---|
| 1 | 0.08 | 5 | 5 | 5 | 5 | 5 | 5 | 5 | 5 | 0 | 5 | 5 |

TABLE 3-continued

| Compound No. | Dose of active ingredient (kg/ha) | Barnyard-grass | Annual sedge | Black night shade | Rorippa spp. | Galinsoga spp. | Rice | Corn | Wheat | Soybean | Cotton | Sugar beet |
|---|---|---|---|---|---|---|---|---|---|---|---|---|
| | 0.16 | 5 | 5 | 5 | 5 | 5 | 5 | 5 | 5 | 0 | 5 | 5 |
| | 0.32 | 5 | 5 | 5 | 5 | 5 | 5 | 5 | 5 | 0 | 5 | 5 |
| 2 | 0.08 | 5 | 5 | 5 | 5 | 4 | 5 | 4 | 5 | 0 | 4 | 5 |
| | 0.16 | 5 | 5 | 5 | 5 | 5 | 5 | 5 | 5 | 0 | 5 | 5 |
| | 0.32 | 5 | 5 | 5 | 5 | 5 | 5 | 5 | 5 | 0 | 5 | 5 |
| 3 | 0.16 | 5 | 5 | 5 | 5 | 5 | 5 | 5 | 5 | 0 | 5 | 5 |
| | 0.32 | 5 | 5 | 5 | 5 | 5 | 5 | 5 | 5 | 0 | 5 | 5 |
| | 0.63 | 5 | 5 | 5 | 5 | 5 | 5 | 5 | 5 | 0 | 5 | 5 |
| 7 | 0.63 | 4 | 2 | 5 | 5 | 5 | 5 | 4 | 1 | 0 | 4 | 5 |
| 15 | 0.08 | 4 | 1 | 4 | 4 | 4 | 3 | 5 | 4 | 0 | 4 | 5 |
| | 0.16 | 5 | 2 | 5 | 5 | 5 | 5 | 5 | 5 | 0 | 5 | 5 |
| | 0.32 | 5 | 3 | 5 | 5 | 5 | 5 | 5 | 5 | 0 | 5 | 5 |
| 26 | 0.63 | 5 | 5 | 5 | 5 | 5 | 5 | 5 | 5 | 0 | 5 | 5 |
| 29 | 0.32 | 5 | 5 | 5 | 5 | 5 | 5 | 5 | 5 | 0 | 0 | 5 |
| | 0.63 | 5 | 5 | 5 | 5 | 5 | 5 | 5 | 5 | 0 | 1 | 5 |
| 50 | 0.32 | 5 | 5 | 5 | 5 | 5 | 5 | 5 | 5 | 0 | 4 | 5 |
| 85 | 0.08 | 5 | 5 | 5 | 5 | 5 | 5 | 5 | 5 | 0 | 5 | 5 |
| | 0.16 | 5 | 5 | 5 | 5 | 5 | 5 | 5 | 5 | 0 | 5 | 5 |
| | 0.32 | 5 | 5 | 5 | 5 | 5 | 5 | 5 | 5 | 1 | 5 | 5 |
| (B)* | 0.32 | 4 | 4 | 5 | 5 | 5 | 2 | 3 | 2 | 1 | 3 | 5 |
| | 1.25 | 4 | 5 | 5 | 5 | 5 | 4 | 5 | 4 | 3 | 5 | 5 |

(B)*: Comparative compound "Acifluorfen-Sodium" (common name) having the following formula:

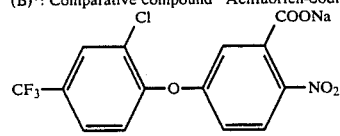

TABLE 4

| Compound No. | Dosage of Active ingredient (kg/ha) | Johnson grass | Barnyard grass | Green foxtail | Goosegrass | Purple nutsedge | Cocklebur | Jimsonweed | Tall morning-glory | Velvet leaf | Prickly sida | Livid amaranth | Hemp sesbania | Soybean |
|---|---|---|---|---|---|---|---|---|---|---|---|---|---|---|
| 1 | 0.16 | 5 | 5 | 5 | 5 | 5 | 5 | 5 | 5 | 5 | 5 | 5 | 3 | 0 |
| | 0.32 | 5 | 5 | 5 | 5 | 5 | 5 | 5 | 5 | 5 | 5 | 5 | 4 | 0 |
| | 0.63 | 5 | 5 | 5 | 5 | 5 | 5 | 5 | 5 | 5 | 5 | 5 | 5 | 0 |
| 2 | 0.16 | 5 | 5 | 5 | 5 | 4 | 5 | 5 | 5 | 5 | 5 | 5 | 4 | 0 |
| | 0.32 | 5 | 5 | 5 | 5 | 5 | 5 | 5 | 5 | 5 | 5 | 5 | 5 | 0 |
| | 0.63 | 5 | 5 | 5 | 5 | 5 | 5 | 5 | 5 | 5 | 5 | 5 | 5 | 0 |
| 3 | 0.16 | 5 | 5 | 5 | 5 | 4 | 5 | 5 | 5 | 5 | 5 | 5 | 4 | 0 |
| | 0.32 | 5 | 5 | 5 | 5 | 5 | 5 | 5 | 5 | 5 | 5 | 5 | 5 | 0 |
| | 0.63 | 5 | 5 | 5 | 5 | 5 | 5 | 5 | 5 | 5 | 5 | 5 | 5 | 0 |
| 15 | 0.16 | 5 | 5 | 5 | 5 | 3 | 5 | 4 | 4 | 4 | 4 | 5 | 4 | 0 |
| | 0.32 | 5 | 5 | 5 | 4 | 4 | 5 | 5 | 5 | 5 | 5 | 5 | 5 | 0 |
| | 0.63 | 5 | 5 | 5 | 5 | 5 | 5 | 5 | 5 | 5 | 5 | 5 | 5 | 0 |
| 85 | 0.16 | 5 | 5 | 5 | 5 | 5 | 5 | 5 | 5 | 5 | 5 | 5 | 5 | 0 |
| | 0.32 | 5 | 5 | 5 | 5 | 5 | 5 | 5 | 5 | 5 | 5 | 5 | 5 | 0 |
| | 0.63 | 5 | 5 | 5 | 5 | 5 | 5 | 5 | 5 | 5 | 5 | 5 | 5 | 1 |
| (B)* | 0.32 | 4 | 4 | 3 | 4 | 1 | 3 | 4 | 4 | 5 | 5 | 5 | 4 | 1 |
| | 0.63 | 5 | 5 | 4 | 5 | 2 | 5 | 5 | 5 | 5 | 5 | 5 | 5 | 2 |

We claim:

1. A compound of the formula:

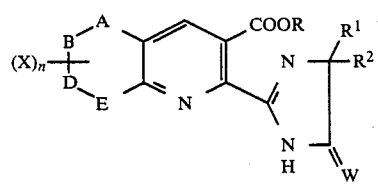

(I)

wherein one of A, B, D, and E is

or =CH— with the rest being all carbon atoms, provided that when one of A, B, D and E is =CH—, one double bond is present in the ring constituted by A, B, D and E, and when one of A, B, D and E is

one double bond may or may not be present in the ring; X is a halogen atom, a $C_1$–$C_4$ alkyl group, a $C_1$–$C_4$ alkoxy group, a $C_1$–$C_4$ chloroalkyl group, a $C_1$–$C_4$ chloroalkoxy group, a $C_1$–$C_4$ alkoxycarbonyl group, a $C_1$–$C_4$ alkylthioalkyl group, a tetrahydrothiopyranyl group, a hydroxyl group, a $CF_3$ group, phenyl or $C_1$–$C_4$ alkylphenyl; n zero, one or two; W is an oxygen atom or a sulfur atom; R is a hydrogen atom, a di-lower alkylimino group, a $C_1$–$C_5$ alkyl group which may be substituted by $C_1$-$C_3$ alkoxy or phenyl which may be substituted by halogen, $C_1$-$C_4$ alkyl, $C_1$-$C_4$ alkoxy or nitro, a $C_2$-$C_5$ alkenyl group which may be substituted by $C_1$-$C_3$ alkoxy, or phenyl, a $C_2$-$C_5$ alkynyl group, a $C_4$ or $C_5$ oxacycloalkyl group, a mono-, di- or tri- chloro -$C_2$-$C_5$ alkenyl group, a chloro -$C_2$-$C_5$ alkynyl group, a glycidyl group, a furfuryl group, an alkylthioalkyl group, a $C_3$-$C_6$ cycloalkyl group which may be substituted by $C_1$-$C_3$ alkyl, or a cation selected from the group consisting of an alkali metal ion, an alkaline earth metal ion, an ammonium ion or a monoalkyl ammonium ion; $R^1$ is a $C_1$-$C_4$ alkyl group, $R^2$ is a $C_1$-$C_4$ alkyl group or a $C_3$-$C_6$ cycloalkyl group, or $R^1$ and $R^2$ together with the adjacent carbon atom form a $C_3$-$C_6$ cycloalkyl group which may be substituted by $C_1$-$C_3$ alkyl.

2. The compound according to claim 1, wherein X is a halogen atom, a $C_1$-$C_4$ alkyl group, a $C_1$-$C_4$ alkoxy group, a $C_1$-$C_4$ chloroalkoxy group or a $CF_3$ group; and R is hydrogen, a $C_1$-$C_5$ alkyl group, a $C_2$-$C_5$ alkenyl group, a $C_2$-$C_5$ alkynyl group, an alkylthioalkyl group or a cation selected from the group consisting of an alkali metal, an alkaline earth metal ion, an ammonium ion or a monoalkyl ammonium ion.

3. The compound according to claim 1, wherein X is a $C_1$-$C_4$ alkyl group or a $C_1$-$C_4$ alkoxy group; and R is hydrogen, a $C_1$-$C_5$ alkyl group, a $C_2$-$C_5$ alkenyl group, a $C_2$-$C_5$ alkynyl group, an alkylthioalkyl group or a cation selected from the group consisting of an alkali metal ion, an alkaline earth metal ion, an ammonium ion or a monoalkyl ammonium ion; $R^1$ is a methyl group and a $R^1$ is an isopropyl group.

4. The compound according to claim 1, which has the formula:

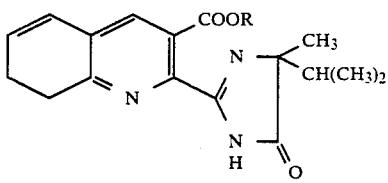

wherein R is a hydrogen atom, a methylthiomethyl group, an alkali metal ion or a monoalkyl ammonium ion.

5. The compound according to claim 4, which has the formula:

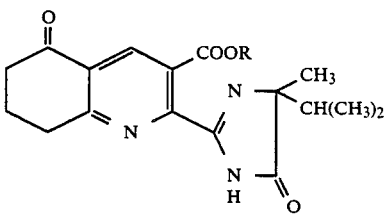

wherein R is a hydrogen atom, a methylthiomethyl group, an alkali metal ion or a monoalkyl ammonium ion.

6. A herbicidal composition comprising a herbicidally effective amount of the compound of claim 1 and a carrier therefor.

7. A method for controlling weeds which comprises applying to the weeds or to the locus of the weeds an effective amount of the compound of claim 1.

* * * * *